United States Patent
Rogers et al.

(10) Patent No.: US 6,174,724 B1
(45) Date of Patent: *Jan. 16, 2001

(54) CHIMERIC GENES SUITABLE FOR EXPRESSION IN PLANT CELLS

(75) Inventors: Stephen G. Rogers, Webster Groves; Robert T. Fraley, Glendale, both of MO (US)

(73) Assignee: Monsanto Company, St. Louis, MO (US)

(*) Notice: Under 35 U.S.C. 154(b), the term of this patent shall be extended for 0 days.

This patent is subject to a terminal disclaimer.

(21) Appl. No.: 08/435,951

(22) Filed: May 4, 1995

Related U.S. Application Data

(62) Division of application No. 08/127,100, filed on Sep. 24, 1993, which is a continuation of application No. 07/732,974, filed on Jul. 19, 1991, now abandoned, which is a continuation of application No. 07/333,802, filed on Apr. 5, 1989, now Pat. No. 5,034,322, which is a continuation of application No. 06/793,488, filed on Oct. 30, 1985, now abandoned, which is a continuation of application No. 06/458,414, filed on Jan. 17, 1983, now abandoned.

(51) Int. Cl.[7] .......................... C12N 15/82; C12N 15/84; C12N 5/04; C12N 15/31

(52) U.S. Cl. .................. 435/419; 435/69.1; 435/70.1; 435/252.2; 435/252.3; 435/252.33; 435/418; 435/469; 536/23.2; 536/23.7; 536/24.1; 536/23.6; 800/288; 800/294

(58) Field of Search .................... 536/23.2, 23.7, 536/24.1, 23.6; 435/69.1, 70.1, 172.3, 240.4, 252.2, 252.3, 252.33, 419, 418, 469; 800/205, 294, 288

(56) References Cited

U.S. PATENT DOCUMENTS

| | | | |
|---|---|---|---|
| 4,536,475 | 8/1985 | Anderson | 435/172.3 |
| 4,886,753 | 12/1989 | Marcker et al. | 435/172.3 |
| 5,034,322 | * 7/1991 | Rogers et al. | 435/172.3 |
| 6,051,757 | 4/2000 | Barton et al. | 800/294 |

FOREIGN PATENT DOCUMENTS

| | | | |
|---|---|---|---|
| WO 82/03087 | 9/1982 | (EP) | C12N/15/00 |
| 83 10 0255 | 1/1983 | (EP) | . |
| 0 131 623 B1 | 1/1984 | (EP) | C12N/15/11 |
| WO 84/02913 | 8/1984 | (EP) | C07H/15/12 |
| 0 290 799 A2 | 11/1988 | (EP) | C12N/15/00 |
| 0 142 924 B1 | 4/1992 | (EP) | C12N/15/05 |

OTHER PUBLICATIONS

Kim et al. Plant Molecular Biology 24:105–117, 1994.*
Marx, J. 1982. Science 216:1305.*
Herrera–Estrella et al. 1983. Nature 303:209–213.*
Barton et al. 1983. Cell 32:1033–1043.*
Fraley et al. 1983. Proc. Natl. Acad. Sci. USA 80:4803–4807.*
DeGreve et al. 1982. Nature 300:752–755.*
Leemans et al. 1982. pp. 537–545 in: Mol. Biol. Plant Tumors, Kahl et al., eds., Academic Press: New York.*
Goodman et al. 1987. Science 236:48–54.*
Lippincott et al. 1978. Science 199:1075–1078.*
Bevan et al. (1983), "A chimaeric antibiotic resistance gene as a selectable marker for plant cell transformation," *Nature* 304:184–187.
Beck et al. (1982) "Nucleotide sequence and exact localization of neomycin phosphotransferase gene from transposon Tn5," *Gene* 19:327–336.
Cairnes et al. (1978) "Translation of animal virus RNA in the cytoplasm of a plant cell," *PNAS* 75(11):5557–5559.
Cairns et al. (1978) "Expression of a DNA Animal Virus Genome in a Plant Cell," *FEBS Letters* 96(2):295–297.
Chilton et al. (1977) "T–DNA from Agrobacterium Ti plasmid is in the nuclear DNA fraction of crown gall tumor cells," *Proc. Natl. Acad. Sci. USA* 77(7):4060–4064.
Chilton et al. (1982) "*Agrobacterium rhizogenes* inserts T–DNA into the genomes of the host plant root cells," *Nature* 295:432–434.
Chilton et al. (1983) "Multiple Viral Specific Transcripts from the Genome of Cauliflower Mosaic Virus," Proceedings of the Miami Winter Symposium, Jan. 1983, published in Advances in Gene Technology: Molecular Genetics of Plants and Animals (Ahmad et al., eds.), p. 564.
Chilton et al. (1983) "Ti and Ri Plasmids as Vectors for Genetic Engineering of Higher Plants," Proceedings of the Miami Winter Symposium, Jan. 1983, published in Advances in Gene Technology: Molecular Genetics of Plants and Animals (Ahmad et al., eds.), pp. 14–15.
Colbere–Garapin et al. (1981) "A New Dominant Hybrid Selective Marker for Higher Eukaryotic Cells," *J. Mol. Biol.* 150:1–14.
Davey et al. (1982) "Transformation in plants: potential and reality," (Abstract of Conference paper from University of Nottingham).
Cocking et al. (1981) "Aspects of plant genetic manipulation," *Nature* 293:265–270.

(List continued on next page.)

Primary Examiner—David T. Fox
(74) Attorney, Agent, or Firm—Lawrence M. Lavin, Jr.; Howrey Simon Arnold & White, L.L.P.

(57) ABSTRACT

This invention relates to chimeric genes which are capable of being expressed in plant cells. Such genes contain (a) a promoter region derived a gene which is expressed in plant cells, such as the nopaline synthase gene; (b) a coding or structural sequence which is heterologous with respect to the promoter region; and (c) an appropriate 3' non-translated region. Such genes have been used to create antibiotic-resistant plant cells; they are also useful for creating herbicide-resistant plants, and plants which contain mammalian polypeptides.

23 Claims, 27 Drawing Sheets

OTHER PUBLICATIONS

DeGreve et al. (1982) "Regeneration of normal and fertile plants that express octopine synthase, from tobacco crown galls after deletion of tumour–controlling functions," *Nature* 300:752–754.

Depicker et al. (1982) "Plant Cell Transformation by Agrobacterium Plasmids," Proceedings of a symposium held Aug. 15–19, 1982 at the University of California, Davis, published in Genetic Engineering of Plants: An Agricultural Perspective, Basic Life Sciences (Kosuge et al., eds. 1983), pp. 143–176.

Dix et al. (1977) "A Cell Line of *Nicotiana sylvestris* with Resistance to Kanamycin and Streptomycin," *Molec. Gen. Genet.* 157:285–290.

Fraley et al. (1983) "Use of a Chimeric Gene to Confer Antibiotic Resistance to Plant Cells," Proceedings of the Miami Winter Symposium, Jan. 1983, published in Advances in Gene Technology, Molecular Genetics of Plants and Animals (Ahmad et al., eds.), pp. 211–221.

Gardner et al. (1982) "Plant Viral Vectors: CaMV As An Experimental Tool," Proceedings of a symposium held Aug. 15–19, 1982 at the University of California, Davis, published in Genetic Engineering of Plants: An Agricultural Perspective, Basic Life Sciences (Kosuge et al., eds. 1983), pp. 121–142.

Garfinkel et al. (1981) "Genetic Analysis of Crown Gall: Fine Structure Map of the T–DNA by Site–Directed Mutagenesis," *Cell* 27:143–153.

Gordon et al. (1983) "Current Developments In The Transformation Of Plants," Proceedings of the Miami Winter Symposium, Jan. 1983, published in Advances in Gene Technology: Molecular Genetics of Plants and Animals (Ahmad et al., eds.), pp. 37–46.

Hall et al. (1983) "The Phaseolin Family of Seed Protein Genes: Sequences and Properties," published in Advances in Gene Technology: Molecular Genetics of Plants and Animals, (Ahmad et al., eds.), pp. 349–367.

Hernalsteens (1980) "The *Agrobacterium tumefaciens* Ti plasmid as a host vector system for introducing foreign DNA in plant cells," *Nature* 287:654–656.

Herrera–Estrella et al. (1983) "Chimeric genes as dominant selectable markers in plant cells," *EMBO J.* 2:987–995.

Hohn et al. (1982) "Cauliflower Mosaic Virus on Its Way to Becoming a Useful Plant Vector," in Current Topics in Microbiology and Immunology, vol. 96 (Henle et al., eds.), pp. 193–236.

Holster et al. (1982) "The Use of Selectable Markers for the Isolation of Plant–DNA/T–DNA Junction Fragments in a Cosmid Vector," *Molec. Gen. Genet.* 185:283–289.

Howell et al. (1980) "Cloned Cauliflower Mosaic Virus DNA Infects Turnips (*Brassica rapa*)," *Science* 208:1265–1267.

Jimenez et al. (1980) "Expression of a transposable antibiotic resistance element in Saccharomyces," *Nature* 287:869–871.

Kemp et al. (1983) "Agrobacterium–Mediated Transfer of Foreign Genes into Plants," in Genetic Engineering: Application to Agriculture (Owens, ed.), pp. 215–228.

Lebeurier et al. (1980) "Infectivities of native and cloned DNA of cauliflower mosaic virus," *Gene* 12:139–146.

Leemans (1982) Universite Libre de Bruxelles, Thesis :1–25, 114–125.

Leemans et al. (1981) "Site–Specific Mutagenesis of Agrobacterium Ti Plasmids and Transfer of Genes to Plant Cells," *J. Molec. Appl. Genet.* 1(2):149–164.

Leemans et al. (1982) "Genetic identification of functions of TL–DNA transcripts in octopine crown galls" *EMBO J.* 1(1):147–152.

Liu et al. (1982) "Agrobacterium Ti plasmic indoleacetic acid gene is required for crown gall oncogenesis," *Proc. Natl. Acad. Sci. USA* 79:2812–2816.

Maliga et al. (1977) "Restoration of Morphogenic Potential in Nicotiana by Somatic Hybridisation," *Molec. Gen. Genet.* 157:291–296.

Marks et al. (1983) "Molecular Structure And Expression Of Maize Zein Genes," published in Advances in Gene Technology: Molecular Genetics of Plants and Animals, pp. 369–381.

Matzke et al. (1981) "Site–Specific Insertion of Genes into T–DNA of the Agrobacterium Tumor–Inducing Plasmid: An Approach to Genetic Engineering of Higher Plant Cells," *J. Molec. Appl. Genet.* 1:39–49.

McKnight et al. (1981) "Isolation and Mapping of Small Cauliflower Mosaic Virus DNA Fragments Active as Promoters in *Escherichia coli,*" *J. Virol.* 37(2):673–682.

Meagher et al. (1980) "A Model for a Molecular Cloning System In Higher Plants: Isolation of Plant Viral Promoters," *NATO Advance Study Institute Series* 29:63–75.

Mulligan et al. (1979) "Synthesis of rabbit β–globin in cultured monkey kidney cells following infection with a SV40 β–globin recombinant genome," *Nature* 277:108–114.

Mulligan et al. (1980) "Expression of a Bacterial Gene in Mammalian Cells" *Science* 209:1422–1427.

Mulligan et al. (1981) "Selection for animal cells that express the *Escherichia coli* gene coding for xanthine–guanine phosphoribosyltransferase," *Proc. Natl. Acad. Sci. USA* 75(4):2072–2076.

O'Hare et al. (1981) "Transformation of mouse fibroblasts to methotrexate resistance by a recombinant plasmid expressing a prokaryotic dihydrofolate reductase," *PNAS* 78(3):1527–1531.

Old et al. (1980) Principles of Gene Manipulation: An Introduction to Genetic Engineering, 1st Ed. (Carr et al., eds.), Univ. of Calif. Press, vol. 2, pp. 9–23.

Old et al. (1981) Principles of Gene Manipulation: An Introduction to Genetic Engineering, 2nd Ed. (Carr et al., eds.), Univ. of Calif. Press, vol. 2, pp. 121–210.

Olszewski et al. (1982) "A Transcriptionally Active, Covalently Closed Minichromosome of Cauliflower Mosaic Virus DNA Isolated from Infected Turnip Leaves," *Cell* 29:395–402.

Otten et al. (1981) "Mendelian Transmission of Genes Introduced into Plants by the Ti Plasmids of *Agrobacterium tumefaciens,*" *Molec. Gen. Genet.* 183:209–213.

Portetelle et al. (1981) "Annales De Gembloux," 87e annee, 3e trimestre, No. 3 :101–123.

Schell et al. (1979) Abstract of "Transfer of genes into plants via the Ti–plasmid of *Agrobacterium tumifaciens,*" Proceedings of a conference held Jul. 3–7, 1978 in Wageningen, Netherlands, published in Broadening the Genetic Base of Crops (Harten et al., eds.), pp. 255–276.

Schell et al. (1982) Abstract of "Plant cell transformation and genetic engineering" published in Plant Improvement and Somatic Cell Genetics (Vasil et al., eds.) Academic Press, NY, pp. 255–276.

Schell et al. (1983) "The Ti Plasmids as Natural and as Practical Gene Vectors for Plants," *Bio/Technology*, Apr. 1983, pp. 175–180.

Schell et al. (1983) "Ti Plasmids As Experimental Gene Vectors For Plants," Proceedings of the Miami Winter Symposium, Jan. 1983, published in Advances in Gene Technology: Molecular Genetics of Plants and Animals (Ahmad et al., eds.), pp. 191–209.

Schroeder et al. (1983) "Ti–Plasmids: Genetic Engineering of Plants," in Plant Cell Culture in Crop Improvement (Sen et al., eds.), Plenum Press, NY, pp. 287–297.

Ursic et al. (1981) "A New Antibiotic With Known Resistance Factors, G418, Inhibits Plant Cells," *Biochem. Biophys. Res. Commun.* 101(3):1031–1037.

Watson (1977) Molecular Biology of the Gene, 3rd Ed., W. A. Benjamin, Inc., Menlo Park, CA, pp. 379–495.

Willmitzer et al. (1980) "DNA from Ti plasmid present in nucleus and absent from plasmids of crown gall plant cells," *Nature* 287:359–361.

Willmitzer et al. (1982) "The TL–DNA in octopine crown–gall tumours codes for seven well–defined polyadenylated transcripts," *EMBO J.* 1(1):139–146.

Barker, et al. (1983) "Nucleotide sequence of the T–DNA region from the *Agrobacterium tumefaciens* Octopine Ti plasmid pTi15955," *Plant Molecular Biology* 2:335–350.

Brisson & Verma (1982) "Soybean leghemoglobin gene family: Normal, pseudo, and truncated genes," *Proc. Natl. Acad. Sci. U.S.A.* 79: 4055–4059.

Franck, et al. (1980) "Nucleotide sequence of cauliflower mosiac virus DNA," *Cell* 21:285–294.

Gardner, et al. (1981) "The complete nucleotide sequences of an infectious clone of cauliflower mosaic virus by M13mp7 shotgun sequencing," *Nucleic Acids Res.* 9: 2871–2888.

Hu, et al. (1982) Primary structure of a genomic zein sequence of maize, *EMBO J.* 1: 1337–1342.

Hyldig–Nielsen, et al. (1982) "The primary structures of two leghemoglobin genes from soybean," *Nucleic Acids Res.* 10:689–701.

Kim, et al. (1994) "A 20 nucleotide upstream element is essential for the nopaline synthase (nos) promoter activity," *Plant Molecular Biology* 24: 105–117.

Kridl, et al. (1984) Nucleotide sequence analysis of a zein genomic clone with a short open reading frame, *Gene* 28: 113–118.

Matzke, et al. (1984) "Transcription of a zein gene introduced into sunflower using a Ti plasmid vector," *EMBO J.* 3:1525–1531.

Messing, et al. (1982) Proceedings of a symposium held Aug. 15–19, 1982 at the University of California, Davis published in Genetic Engineering Of Plants: An Agricultural Perspective, Basic Life Sciences 26: 211–227 (Kosuge, et al., eds. 1983).

Pedersen, et al. (1982) "Cloning and sequence analysis reveal structural variation among related zein genes in maize," *Cell* 29: 1015–1026.

Shah, et al. (1982) "Complete nucleotide sequence of a soybean actin gene," *Proc. Natl. Acad. Sci. U.S.A.* 79: 1022–1026.

Velten, et al. (1983) *Molecular Genetics of the Bacteria–Plant Interaction*, Verlag, Berlin, Puhler, A. (ed.) pp. 303–312.

Wiborg, et al. (1982) "The nucleotide sequences of two leghemoglobin genes from soybean," *Nucleic Acids Res.* 10: 3487–3494.

Flavell et al., *Bio/Technology*, 10: 141–144 (1992). Selectable marker genes: safe for plants?.

Leemans, *Bio/Technology* 11: S22–S26 (1993). Ti to tomato, tomato to market.

Messing et al., Proceedings of Symposium held Aug. 15–19, 1982 at the University of California, Davis, published in Basic Life Sciences, 26: 211–227 (1983). Plant gene structure.

Barker et al. *Plant Molecular Biology*, 2:335–350 (1983). Nucleotide sequence of the T–DNA region from the *Agrobacterium tumefaciens* Octopine Ti plasmid pTi15955.

De Greve et al., *J. Mol. Appl. Genet.*, 1,6: 499–511 (1982). Nucleotide sequence and transcript map of the *Agrobacterium tumefaciens* Ti plasmid–encoded octopine synthase gene.

Velten et al., *Molecular Genetics of the Bacteria–Plant Interaction*, Verlag, Berlin, Puhler, A. (ed.) 303–312 (1983). $T_R$ genes involved in agropine production.

Bedbrook et al., *Nature*, 287: 692–697 (1980). Molecular cloning and sequencing of cDNA encoding the percursor to the small subunit of chloroplast ribulose–1,5–bisphosphate carboxylase.

Wimpee et al., *Plant Molecular Biology*, Arco Solar—UCLA Symposium, Apr. 16–22, 1983, pp. 391–401. Sequence heterogeneity in the RuBP carboxylase small subunit gene family of *Lemna Gibba*.

Berry–Lowe et al., *J. Mol. Appl. Genet.*, 1,6: 483–498 (1982). The nucleotide sequence, expression, and evolution of one member of a multigene family encoding the small subunit of Ribulose–1,5–biphosphate carboxylase in . . . .

Broglie et al., *Bio/Technology*, 55–61 (1983). Structural analysis of nuclear genes coding for the precursor to the small subunit of wheat ribulose–1,5–biphosphate carboxylase.

Broglie et al., *Science*, 224: 838–843 (1984). Light–regulated expression of a pea ribulose–1,5–biphosphate carboxylase small subunit gene in transformed plant cells.

Timko et al., *Plant Molecular Biology*, Arco Solar—UCLA Symposium, Apr. 16–22, 1983, pp. 403–412. Nuclear genes encoding the constituent polypeptides of the light–harvesting chlorophyll A/B–protein complex . . . .

Geraghty et al., *Nucl. Acids Res.*, vol. 9, 19: 5163–5174 (1981). The primary structure of a plant storage protein: zein.

Pedersen et al., *Cell*, 29: 1015–1026 (1982). Cloning and sequence analysis reveat structural variation among related zein genes in maize.

pg,13

Fischer et al., *Cell*, 29: 651–660 (1982). Structure and flanking regions of soybean seed protein genes.

Beachy et al., *Plant Molecular Biology*, Arco Solar—UCLA Symposium, Apr. 16–22, 1983, pp. 413–422. Molecular characterization of a soybean variety lacking a subunit of the 7S seed storage protein.

Beachy et al., *EMBO J.*, 4,12: 3047–3053 (1985). Accumulation and assembly of soybean β–conglycimin in seeds of transformed petunia plants.

Shah et al., *PNAS USA,* 79: 1022–1026 (1982). Complete nucleotide sequence of a soybean actin gene.

Meagher et al., Advances in Gene Technology: Molecular Genetics of Plants and Animals, Miami Winter Symposia, vol. 20, pp. 171–187 (1983). Plant actin is encoded by diverse multigene families.

Sun et al., *Nature,* 289: 37–41 (1981). Intervening sequences in a plant gene–comparison of the partial sequence of a cDNA and genomic DNA of French bean phaseolin. pg,14

Slightom et al., *PNAS USA,* 80: 1897–1901 (1983). Complete nucleotide sequence of a French bean storage protein gene: Phaseolin.

Murai et al., *Science,* 222: 476–482 (1983). Phaseolin gene from bean is expressed after transfer to sunflower via tumor–inducing plasmid vectors.

Gerlach et al., *PNAS USA,* 79: 2981–2985 (1982). cDNA cloning and induction of the alcohol dehydrogenase gene (Adh1) of maize.

Peacock et al., Advances in Gene Technology: Molecular Genetics of Plants and Animals, Miami Winter Symposia, vol. 20, pp. 311–325 (1983). Gene transfer in maize: controlling elements and the alcohol . . . .

Lee et al., *Plant Molecular Biology,* Arco Solar—UCLA Symposium, Apr. 16–22, 1983, pp. 355–365. Control of tuber protein synthesis in potato.

Schoffl et al., *J. Mol. Appl. Genet.,* 1: 301–314 (1982). An analysis of mRNAs for a group of heat shock proteins of soybean using cloned cDNAs.

\* cited by examiner

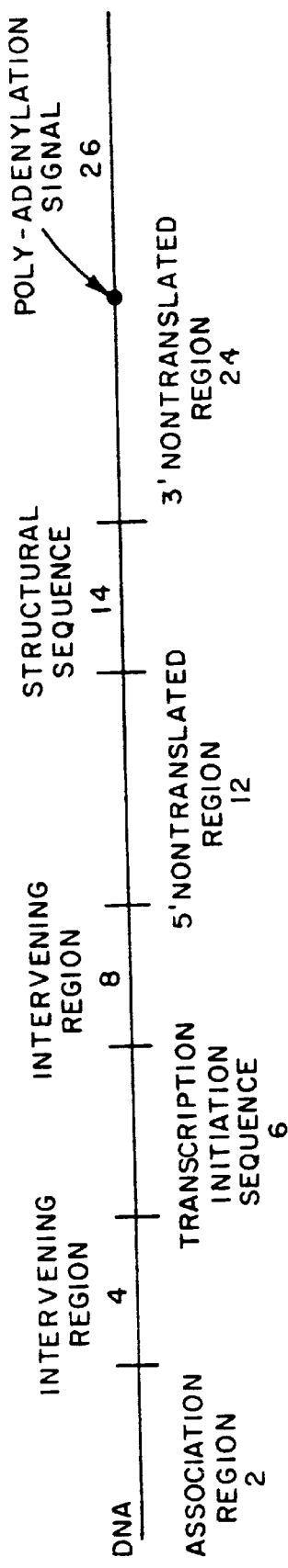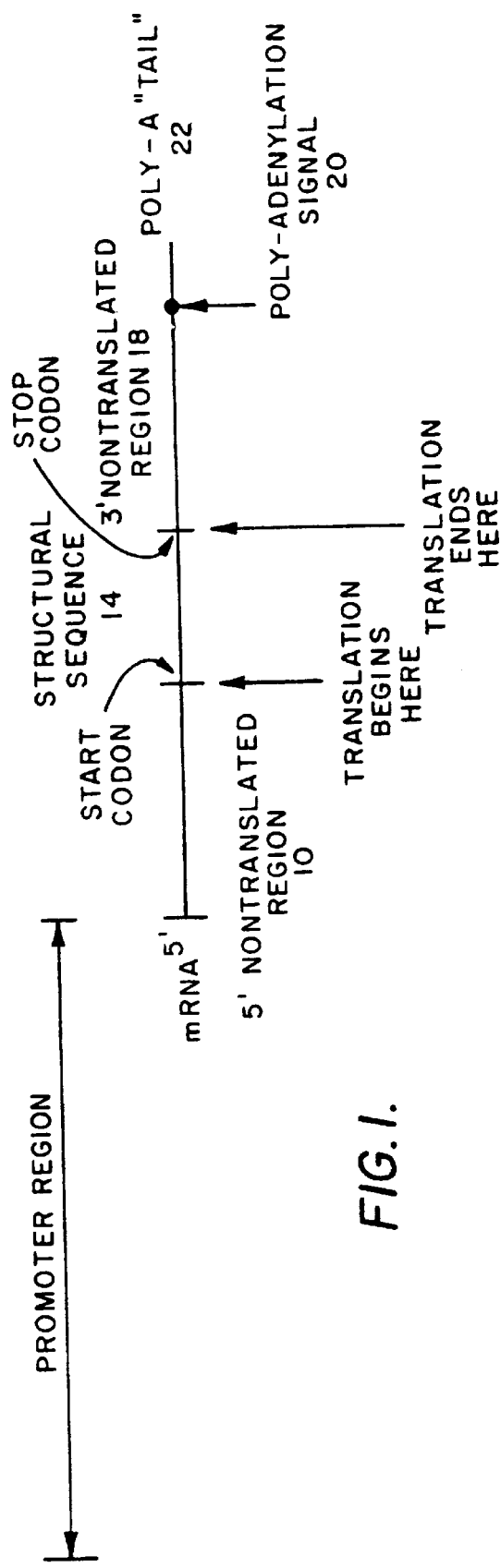
FIG. 1.

Sau3a FRAGMENT CONTAINING
NOS PROMOTER REGION
(ANTI-SENSE STRAND, 344bp)

```
Sau3a
   v       10              20              30              40              50
5'- TGATCATGAG    CGGAGAATTA    AGGGAGTCAC    GTTATGACCC    CCGCCGATGA 60              70              80              90              100
CGCGGGACAA    GCCGTTTTAC    GTTTGGAACT    GACAGAACCG    CAACGTTGAA

SstII
    110     v 120             130             140             150
GGAGCCACTC    AGCCGCGGGT    TTCTGGAGTT    TAATGAGCTA    AGCACATACG 160             170             180             190             200
TCAGAAACCA    TTATTGCGCG    TTCAAAAGTC    GCCTAAGGTC    ACTATCAGCT 210             220             230             240             250
AGCAAATATT    TCTTGTCAAA    AATGCTCCAC    TGACGTTCCA    TAAATTCCCC 260             270             280             290             300
TCGGTATCCA    ATTAGAGTCT    CATATTCACT    CTCAATCCAA    ATAATCTGCA
                              ↑                    3'- GGTT    TATTAGACGT ─╮
                         mRNA 5' END                  Synthetic           5'
                                                       Primer
    310             320             330             340
ATGGCAATTA    CCTTATACCGC    AACTTCTTTA    CCTATTTCCG    CCGCAGATC
                                                              ^
 ↑  NOS STRUCTURAL                                           Sau3a
START  SEQUENCE
CODON
```

FIG. 4.

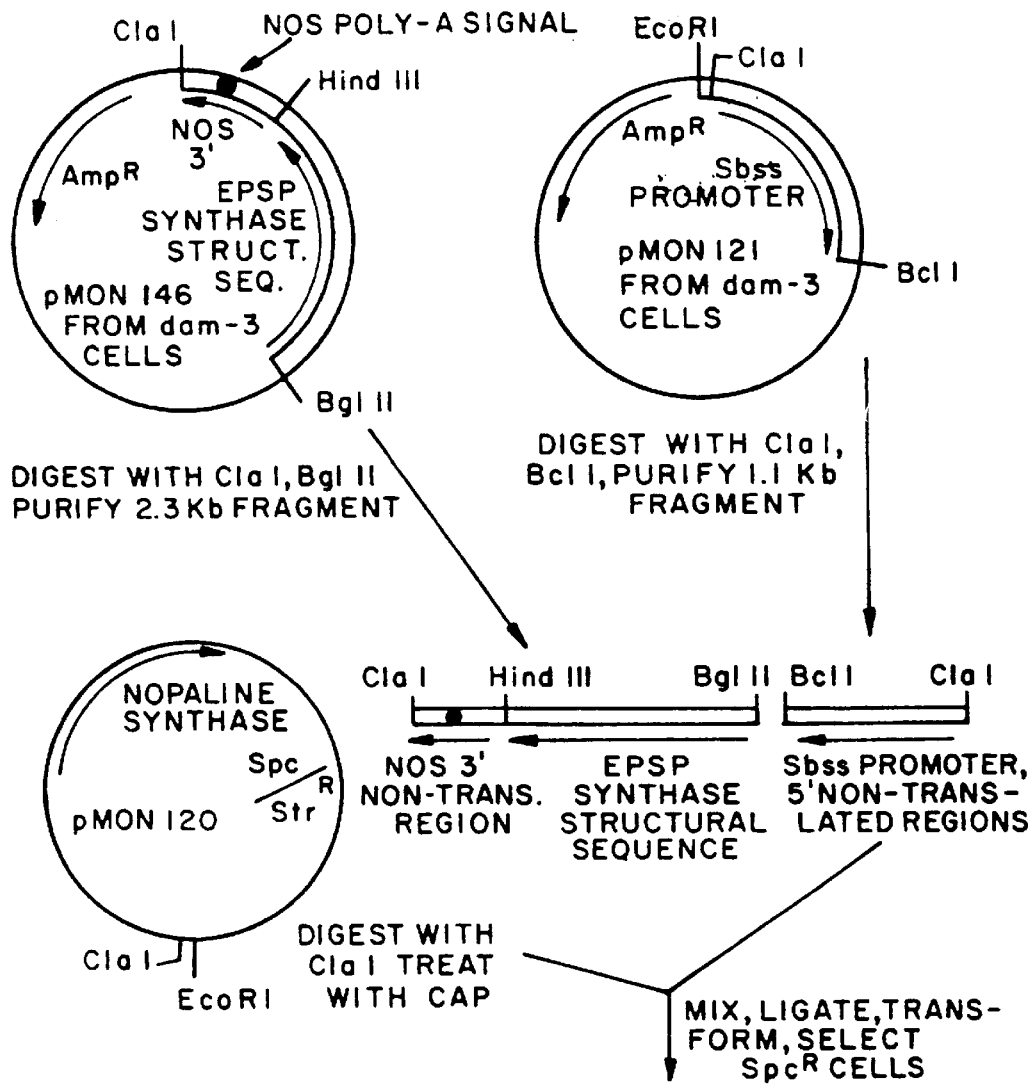
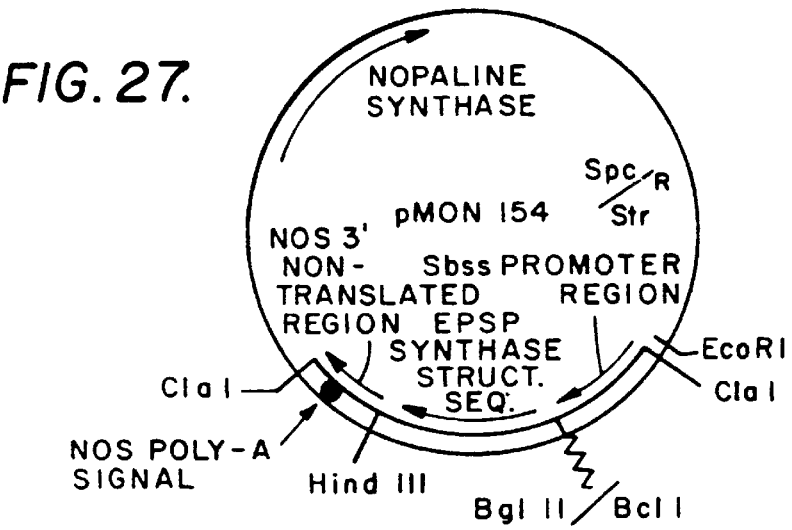
FIG. 27.

CHIMERIC GENES SUITABLE FOR EXPRESSION IN PLANT CELLS

This is a Divisional of U.S. application Ser. No. 08/127,100, filed Sep. 24, 1993, which is a File Wrapper Continuation of U.S. application Ser. No. 07/732,974, filed Jul. 19, 1991, now abandoned, which is a Continuation of application Ser. No. 07/333,802, filed Apr. 5, 1989, now U.S. Pat. No. 5,034,322, which is a Continuation of U.S. application Ser. No. 06/793,488, filed Oct. 30, 1985, now abandoned, which is a Continuation of U.S. application Ser. No. 06/458,414 filed Jan. 17, 1983, now abandoned.

TECHNICAL FIELD

This invention is in the fields of genetic engineering, plant biology, and bacteriology.

BACKGROUND ART

In the past decade, the science of genetic engineering has developed rapidly. A variety of processes are known for inserting a heterologous gene into bacteria, whereby the bacteria become capable of efficient expression of the inserted genes. Such processes normally involve the use of plasmids which may be cleaved at one or more selected cleavage sites by restriction endonucleases, discussed below. Typically, a gene of interest is obtained by cleaving one piece of DNA and the resulting DNA fragment is mixed with a fragment obtained by cleaving a vector such as a plasmid. The different strands of DNA are then connected ("ligated") to each other to form a reconstituted plasmid. See, for example, U.S. Pat. No. 4,237,224 (Cohen and Boyer, 1980); U.S. Pat. No. 4,264,731 (Shine, 1981); U.S. Pat. No. 4,273,875 (Manis, 1981); U.S. Pat. No. 4,322,499 (Baxter et al., 1982), and U.S. Pat. No. 4,336,336 (Silhavy et al., 1982). A variety of other reference works are also available. Some of these works describe the natural processes whereby DNA is transcribed into messenger (mRNA) and mRNA is translated into protein; see, e.g., Stryer, 1981 (note: all references cited herein, other than patents, are listed with citations after the Examples); Lehninger, 1975. Other works describe methods and products of genetic manipulation; see, e.g., Maniatis et al., 1982; Setlow and Hollaender, 1979.

Most of the genetic engineering work performed to date involves the insertion of genes into various types of cells primarily bacteria such as *E. coli*, various other types of microorganisms such as yeast, and mammalian cells. However, many of the techniques and substances used for genetic engineering of animal cells and microorganisms are not directly applicable to genetic engineering involving plants.

As used herein, the term "plant" refers to a multicellular differentiated organism that is capable of photosynthesis, such as angiosperms and multicellular algae. This does not include microorganisms, such as bacteria, yeast, and fungi. However, the term "plant cells" includes any cell derived from a plant; this includes undifferentiated tissue such as callus or crown gall tumor, as well as plant seeds, propagules, pollen, and plant embryos.

A variety of plant genes have been isolated, some of which have been published and/or are publicly available. Such genes include the soybean actin gene (Shah et al., 1982), corn zein (Pederson et al., 1982) soybean leghemoglobin (Hyldig-Nielsen et al., 1982), and soybean storage proteins (Fischer and Goldberg, 1982).

The Reigons of a Gene

The expression of a gene involves the creation of a polypeptide which is coded for by the gene. This process involves at least two steps: part of the gene is transcribed to form messenger RNA, and part of the mRNA is translated into a polypeptide. Although the processes of transcription and translation are not fully understood, it is believed that the transcription of a DNA sequence into mRNA is controlled by several regions of DNA. Each region is a series of bases (i.e., a series of nucleotide residues comprising adenosine (A), thymidine (T), cytidine (C), and guanidine (G)) which are in a desired sequence. Regions which are usually present in a eucaryotic gene are shown on FIG. 1. These regions have been assigned names for use herein, and are briefly discussed below. It should be noted that a variety of terms are used in the literature, which describes these regions in much more detail.

An association region 2 causes RNA polymerase to associate with the segment of DNA. Transcription does not occur at association region 2; instead, the RNA polymerase normally travels along an intervening region 4 for an appropriate distance, such as about 100–300 bases, after it is activated by association region 2.

A transcription initiation sequence 6 directs the RNA polymerase to begin synthesis of mRNA. After it recognizes the appropriate signal, the RNA polymerase is believed to begin the synthesis of mRNA an appropriate distance, such as about 20 to about 30 bases, beyond the transcription initiation sequence 6. This is represented in FIG. 1 by intervening region 8.

The foregoing sequences are referred to collectively as the promoter region of the gene.

The next sequence of DNA is transcribed by RNA polymerase into messenger RNA which is not translated into protein. In general, the 5' end of a strand of mRNA attaches to a ribosome. In bacterial cells, this attachment is facilitated by a sequence of bases called a "ribosome binding site" (RBS). However, in eucaryotic cells, no such RBS sequence is known to exist. Regardless of whether an RBS exists in a strand of mRNA, the mRNA moves through the ribosome until a "start codon" is encountered. The start codon is usually the series of three bases, AUG; rarely, the codon GUG may cause the initiation of translation. The non-translated portion of mRNA located between the 5' end of the mRNA and the start codon is referred to as the 5' non-translated region 10 of the mRNA. The corresponding sequence in the DNA is also referred to herein as 5' non-translated region 12. The specific series of bases in this sequence is not believed to be of great importance to the expression of the gene; however, the presence of a premature start codon might affect the translation of the mRNA (see Kozak, 1978).

A promoter sequence may be significantly more complex than described above; for example, certain promoters present in bacteria contain regulatory sequences that are often referred to as "operators." Such complex promoters may contain one or more sequences which are involved in induction or repression of the gene. One example is the lac operon, which normally does not promote transcription of certain lactose-utilizing enzymes unless lactose is present in the cell. Another example is the trp operator, which does not promote transcription or translation of certain tryptophan-creating enzymes if an excess of tryptophan is present in the cell. See, e.g., Miller and Reznikoff, 1982.

The next sequence of bases is usually called the coding sequence or the structural sequence 14 (in the DNA molecule) or 16 (in the mRNA molecule). As mentioned above, the translation of a polypeptide begins when the mRNA start codon, usually AUG, reaches the translation mechanism in the ribosome. The start codon directs the ribosome to begin connecting a series of amino acids to each other by peptide bonds to form a polypeptide, starting with methionine, which always forms the amino terminal end of the polypeptide (the methionine residue may be subsequently removed from the polypeptide by other enzymes). The bases which follow the AUG start codon are divided into sets of 3, each of which is a codon. The "reading frame," which specifies how the bases are grouped together into sets of 3, is determined by the start codon. Each codon codes for the addition of a specific amino acid to the polypeptide being formed. The entire genetic code (there are 64 different codons) has been solved; see, e.g., Lehninger, supra, at p. 962. For example, CUA is the codon for the amino acid leucine; GGU specifies glycine, and UGU specifies cysteine.

Three of the codons (UAA, UAG, and UGA) are "stop" codons; when a stop codon reaches the translation mechanism of a ribosome, the polypeptide that was being formed disengages from the ribosome, and the last preceding amino acid residue becomes the carboxyl terminal end of the polypeptide.

The region of mRNA which is located on the 3' side of a stop codon in a monocistronic gene is referred to herein as 3' non-translated region 18. This region is believed to be involved in the processing, stability, and/or transport of the mRNA after it is transcribed. This region 18 is also believed to contain a sequence polyadenylation signal 20, which is recognized by an enzyme in the cell. This enzyme adds a substantial number of adenosine residues to the mRNA molecule, to form poly-A tail 22.

The DNA molecule has a 3' non-translated region 24 and a polyadenylation signal 26, which code for the corresponding mRNA region 18 and signal 20. However, the DNA molecule does not have a poly-A tail. Polyadenylation signals 20 (mRNA) and 26 (DNA) are represented in the figures by a heavy dot.

Gene-Host Incompatibility

The same genetic code is utilized by all living organisms on Earth. Plants, animals, and microorganisms all utilize the same correspondence between codons and amino acids. However, the genetic code applies only to the structural sequence of a gene, i.e., the segment of mRNA bounded by one start codon and one stop codon which codes for the translation of mRNA into polypeptides.

However, a gene which performs efficiently in one type of cell may not perform at all in a different type of cell. For example, a gene which is expressed in *E. coli* may be transferred into a different type of bacterial cell, a fingus, or a yeast. However, the gene might not be expressed in the new host cell. There are numerous reasons why an intact gene which is expressed in one type of cell might not be expressed in a different type of cell. See, e.g., Sakaguchi and Okanishi, 1981. Such reasons include:

1. The gene might not be replicated or stably inherited by the progeny of the new host cell.

2. The gene might be broken apart by restriction endonucleases or other enzymes in the new host cell.

3. The promoter region of the gene might not be recognized by the RNA polymerases in the new host cell.

4. One or more regions of the gene might be bound by a repressor protein or other molecule in the new host cell, because of a DNA region which resembles an operator or other regulatory sequence of the host's DNA. For example, the lac operon includes a polypeptide which binds to a particular sequence of bases next to the lac promoter unless the polypeptide is itself inactivated by lactose. See, e.g., Miller and Reznikoff, 1982.

5. One or more regions of the gene might be deleted, reorganized, or relocated to a different part of the host's genome. For example, numerous procaryotic cells are known to contain enzymes which promote genetic recombination (such as the rec proteins in *E. coli*; see, e.g., Shibata et al., 1979) and transposition (see, e.g., The 45th Cold Spring Harbor Symposium on Quantitative Biology, 1981). In addition, naturally-occurring genetic modification can be enhanced by regions of homology between different strands of DNA; see, e.g., Radding, 1978.

6. mRNA transcribed from the gene may suffer from a variety of problems. For example, it might be degraded before it reaches the ribosome, or it might not be polyadenylated or transported to the ribosome, or it might not interact properly with the ribosome, or it might contain an essential sequence which is deleted by RNA processing enzymes.

7. The polypeptide which is created by translation of the mRNA coded for by the gene may suffer from a variety of problems. For example, the polypeptide may have a toxic effect on the cell, or it may be glycosylated or converted into an altered polypeptide, or it may be cleaved into shorter polypeptides or amino acids, or it may be sequestered within an intracellular compartment where it is not functional.

In general, the likelihood of a foreign gene being expressed in a cell tends to be lower if the new host cell is substantially different from the natural host cell. For example, a gene from a certain species of bacteria is likely to be expressed by other species of bacteria within the same genus. The gene is less likely to be expressed by bacteria of a different genus, and even less likely to be expressed by non-bacterial microorganisms such as yeast, fungus, or algae. It is very unlikely that a gene from a cell of one kingdom (the three kingdoms are plants, animals, and "protista" (microorganisms)) could be expressed in cells from either other kingdom.

These and other problems have, until now, thwarted efforts to obtain expression of foreign genes into plant cells. For example, several research teams have reported the insertion of foreign DNA into plant cells; see, e.g., Lurquin, 1979; Krens et al., 1982; Davey et al., 1980. At least three teams of researchers have reported the insertion of entire genes into plant cells. By use of radioactive DNA probes, these researchers have reported that the foreign genes (or at least portions thereof) were stably inherited by the descendants of the plant cells. See Hernalsteens et al., 1980; Garfinkel et al., 1981; Matzke and Chilton, 1981. However, there was no reported evidence that the foreign genes were expressed in the plant cells.

Several natural exceptions to the gene-host incompatibility barriers have been discovered. For example, several *E. coli* genes can be expressed in certain types of yeast cells, and vice-versa. See Beggs, 1978; Struhl et al., 1979.

In addition, certain types of bacterial cells, including *Agrobacterium tumefaciens* and *A. rhizogenes*, are capable of infecting various types of plant cells, causing plant diseases such as crown gall tumor and hairy root disease. These Agrobacterium cells carry plasmids, designated as Ti plasmids and Ri plasmids, which carry genes which are expressed in plant cells. Certain of these genes code for enzymes which create substances called "opines," such as octopine, nopaline, and agropine. Opines are utilized by the bacteria cells as sources of carbon, nitrogen, and energy. See, e.g., Petit and Tempe, 1978. The opine genes are believed to be inactive while in the bacterial cells; these genes are expressed only after they enter the plant cells.

In addition, a variety of man-made efforts have been reported to overcome one or more of the gene-host incompatibility barriers. For example, it has been reported that a mammalian polypeptide which is normally degraded within a bacterial host can be protected from degradation by coupling the mammalian polypeptide to a bacterial polypeptide that normally exists in the host cell. This creates a "fusion protein;" see, e.g., Itakura et al., 1977. As another example, in order to avoid cleavage of an inserted gene by endonucleases in the host cell, it is possible to either (1) insert the gene into host cells which are deficient in one or more endonucleases, or (2) duplicate the gene in cells which cause the gene to be methylated. See, e.g., Maniatis et al., 1981.

In addition, various efforts to overcome gene-host incompatibility barriers involve chimeric genes. For example, a structural sequence which codes for a mammalian polypeptide, such as insulin, interferon, or growth hormone, may be coupled to regulatory sequences from a bacterial gene. The resulting chimeric gene may be inserted into bacterial cells, where it will express the mammalian polypeptide. See, e.g., Guarente et al., 1980. Alternately, structural sequences from several bacterial genes have been coupled to regulatory sequences from viruses which are capable of infecting mammalian cells. The resulting-chimeric genes were inserted into mammalian cells, where they reportedly expressed the bacterial polypeptide. Southern and Berg, 1982; Colbere-Garapin et al., 1981.

Restriction Endonucleases

In general, an endonuclease is an enzyme which is capable of breaking DNA into segments of DNA. An endonuclease is capable of attaching to a strand of DNA somewhere in the middle of the strand, and breaking it. By comparison, an exonuclease removes nucleotides, from the end of a strand of DNA. All of the endonucleases discussed herein are capable of breaking double-stranded DNA into segments. This may require the breakage of two types of bonds: (1) covalent bonds between phosphate groups and deoxyribose residues, and (2) hydrogen bonds (A-T and C-G ) which hold the two strands of DNA to each other.

A "restriction endonuclease" (hereafter referred to as an endonuclease) breaks a segment of DNA at a precise sequence of bases. For example, EcoRI and HaeIII recognize and cleave the following sequences:

```
EcoRI:  5'- G|AATTC  ⟶   XXG    + AATTCXX
            CTTAA|G-5'    YYCTTAA     GYY

HaeIII: 5'- GG|CC   ⟶   XXGG   + CCXX
            CC|GG       YYCC   + GGYY
```

In the examples cited above, the EcoRI cleavage created a "cohesive" end with a 5' overhang (i.e., the single-stranded "tail" has a 5' end rather than a 3' end). Cohesive ends can be useful in promoting desired ligations. For example, an EcoRI end is more likely to anneal to another EcoRI end than to a HaeIII end.

Over 100 different endonucleases are known, each of which is capable of cleaving DNA at specific sequences. See, e.g., Roberts, 1982. All restriction endonucleases are sensitive to the sequence of bases. In addition, some endonucleases are sensitive to whether certain bases have been methylated. For example, two endonucleases, MboI and Sau3a are capable of cleaving the following sequence of bases as shown:

```
5-XX|GATCXX  ⟶   5'-XX    + GATCXX
  YYCTAG|YY       YYCTAG     YY
```

MboI cannot cleave this sequence if the adenine residue is methylated (me-A). Sau3a can cleave this sequence, regardless of whether either A is methylated. To some extent the methylation (and therefore the cleavage) of a plasmid may be controlled by replicating the plasmids in cells with desired methylation capabilities. An *E. coli* enzyme, DNA adenine methylase (dam), methylates the A residues that occur in GATC sequences. Strains of *E. coli* which do not contain the dam enzyme are designated as dam-cells. Cells which contain dam are designated as dam⁺ cells.

Several endonucleases are known which cleave different sequences, but which create cohesive ends which are fully compatible with cohesive ends created by other endonucleases. For example, at least five different endonucleases create 5' GATC overhangs, as shown in Table 1.

TABLE 1

| Endonuclease | Sequence |
|---|---|
| MboI<br>Inhibited by me-A | \|GATC<br>CTAG\| |
| Sau3a<br>Unaffected by me-A | same as MooI |
| BglII<br>Unaffected by me-A | A\|GATCT<br>TCTAG\|A |
| BclI<br>Inhibited by me-A | T\|GATCA<br>ACTAG\|T |
| BamHI<br>Unaffected by me-A | G\|GATCC<br>CCTAG\|G |

A cohesive end created by any of the endonucleases listed in Table 1 will ligate preferentially to a cohesive end created by any of the other endonucleases. However, a ligation of, for example, a BglII end with a BamHI end will create the following sequence:

```
AGATCC
TCTAGG
```

This sequence cannot be cleaved by either Bgl II or BamHI; however, it can be cleaved by MboI (unless methylated) or by Sau3a.

Another endonuclease which involves the GATC sequence is PvuI, which creates a 3' overhang, as follows:

```
OGAT|CG
GC|TAGC
```

Another endonuclease, ClaI, cleaves the following sequence:

```
X₁AT|CGATX₂
Y TAGC|TAY
```

If $X_1$ is G, or if $X_2$ is C, then the sequence may be cleaved by MboI (unless methylated, in which case ClaI is also inhibited) or Sau3a.

SUMMARY OF THE INVENTION

This invention relates to chimeric genes which are capable of being expressed in plant cells, and to a method for creating such genes.

The chimeric gene comprises a promoter region which is capable of causing RNA polymerase in a plant cell to create messenger RNA corresponding to the DNA. One such promoter region comprises a nopaline synthase (NOS) promoter region, which normally exists in certain types of Ti plasmids in bacteria, A. tumefaciens. The NOS gene normally is inactive while contained in A. tumefaciens cells, and it becomes active after the Ti plasmid enters a plant cell. Other suitable promoter regions may be derived from genes which exist naturally in plant cells.

The chimeric gene also contains a sequence of bases which codes for a 5' non-translated region of mRNA which is capable of enabling or increasing the expression in a plant cell of a structural sequence of the mRNA. For example, a suitable 5' non-translated region may be taken from the NOS gene mentioned above, or from a gene which exists naturally in plant cells.

The chimeric gene also contains a desired structural sequence, i.e., a sequence which is transcribed into mRNA which is capable of being translated into a desired polypeptide. The structural sequence is heterologous with respect to the promoter region, and it may code for any desired polypeptide, such as a bacterial or mammalian protein. The structural sequence includes a start codon and a stop codon. The structural sequence may contain introns which are removed from the mRNA prior to translation.

If desired, the chimeric gene may also contain a DNA sequence which codes for a 3' non-translated region (including a poly-adenylation signal) of mRNA. This region may be derived from a gene which is naturally expressed in plant cells, to help ensure proper expression of the structural sequence. Such genes include the NOS gene mentioned above, as well as genes which exist naturally in plant cells.

The method of this invention is described below, and is summarized in the flow chart of FIG. 2.

If properly assembled and inserted into a plant genome, a chimeric gene of this invention will be expressed in the plant cell to create a desired polypeptide, such as a mammalian hormone, or a bacterial enzyme which confers antibiotic or herbicide resistance upon the plant.

BRIEF DESCRIPTION OF THE DRAWINGS

The figures herein are schematic representations; they have not been drawn to scale.

FIG. 1 represents the structure of a typical eukaryotic gene.

FIG. 4 represents a DNA fragment which contains a NOS promoter region, a NOS 5' non-translated region, and the first few codons of the NOS structural sequence.

FIG. 27 represents the creation of plasmid pMON154, which contains a chimeric sbss-EPSP-NOS gene.

DETAILED DESCRIPTION OF THE INVENTION

In one preferred embodiment of this invention, a chimeric gene was created which contained the following elements:

1. A promoter region and a 5' non-translated region derived from a nopaline synthase (NOS) gene;

2. A structural sequence derived from a neomycin phosphotransferase II (NPTII) gene; and, 3. A 3' non-translated region, including a poly-adenylation signal, derived from a NOS gene.

This chimeric gene, referred to herein as a NOS-NPTII-NOS gene, was assembled and inserted into a variety of plant cells, causing them to become resistant to aminoglycoside antibiotics such as kanamycin.

Figure 2:
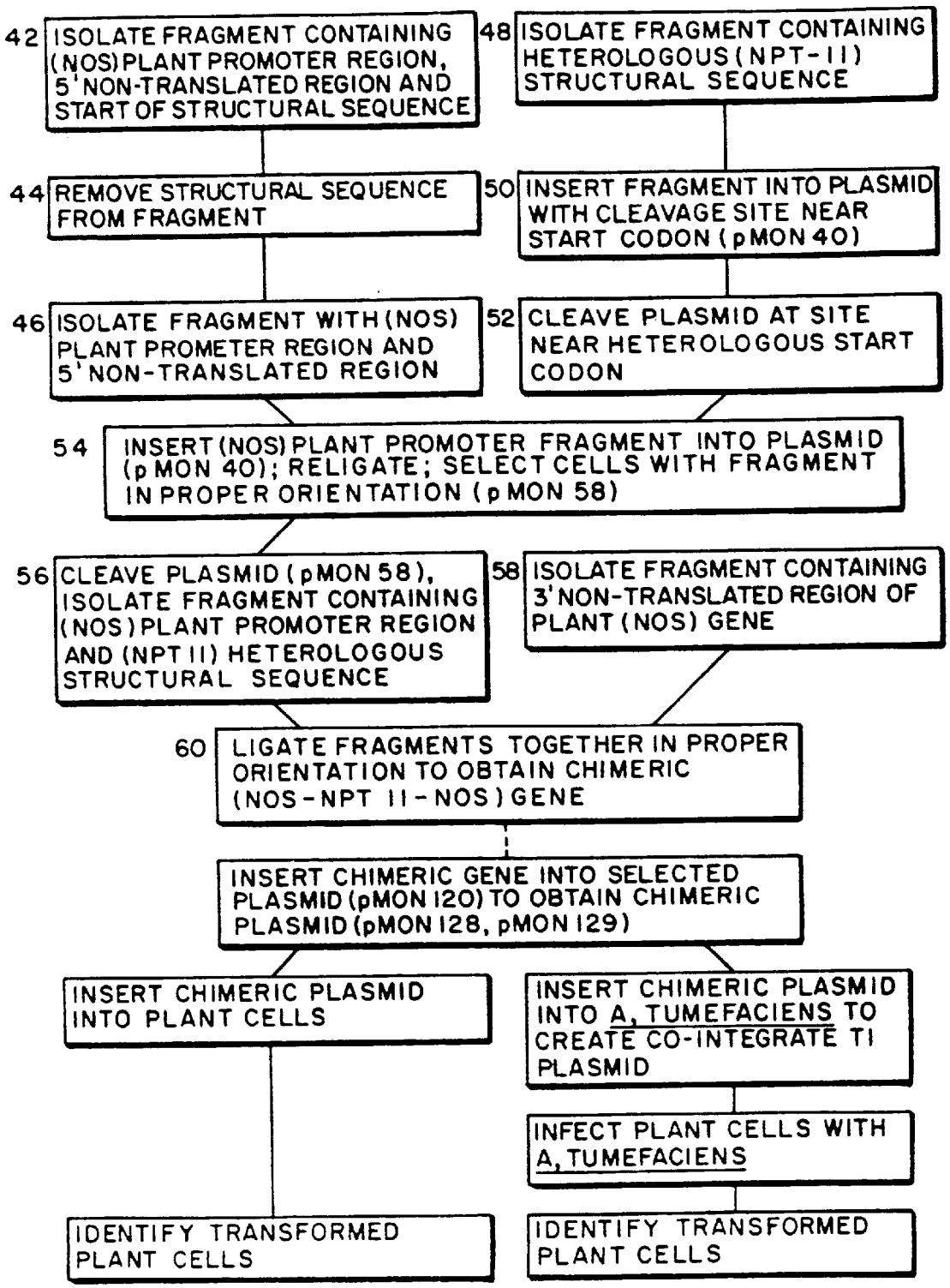
FIG. 2 is a flow chart representing the steps of this invention, correlated with an example chimeric NOS-NPTII-NOS gene.

The method used to assemble this chimeric gene is summarized in the flow chart of FIG. 2, and described in detail below and in the examples. To assist the reader in understanding the steps of this method, various plasmids and fragments involved in the NOS-NPTII-NOS chimeric gene are cited in parentheses in FIG. 2. However, the method of FIG. 2 is applicable to a wide variety of other plasmids and fragments. To further assist the reader, the steps shown in FIG. 2 have been assigned callout numbers 42 et seq. These callout numbers are cited in the following description. The techniques and DNA sequences of this invention are likely to be useful in the transformation of a wide variety of plants, including any plant which may be infected by one or more strains of *A. tumefaciens* or *A. rhizogenes*.

The NOS Promoter Region and 5' Non-translated Region

The Applicants decided to obtain and utilize a nopaline synthase (NOS) promoter region to control the expression of the heterologous gene. The NOS is normally carried in certain types of Ti plasmids, such as pTiT37. Sciaky et al., 1978. The NOS promoter is normally inactive while in an *A. tumefaciens* cell. The entire NOS gene, including the promoter and the protein coding sequence, is within the T-DNA portion of a Ti plasmid that is inserted into the chromosomes of plant cells when a plant becomes infected and forms a crown gall tumor. Once inside the plant cell, the NOS promoter region directs RNA polymerase within a plant cell to transcribe the NOS protein coding sequence into mRNA, which is subsequently translated into the NOS enzyme.

The boundaries between the different parts of a promoter region (shown in FIG. 1 as association region 2, intervening region 4, transcription initiation sequence 6, and intervening region 8), and the boundary between the promoter region and the 5' non-translated region, are not fully understood. The Applicants decided to utilize the entire promoter region and 5' non-translated region from the NOS gene, which is known to be expressed in plant cells. However, it is entirely possible that one or more of these sequences might be modified in various ways, such as alteration in length or replacement by other sequences. Such modifications in promoter regions and 5' non-translated regions have been studied in bacterial cells (see, e.g., Roberts et al 1979) and mammalian cells (see, e.g., McKnight, 1982). By utilizing the methodology taught by this invention, it is now possible to study the effects of modifications to promoter regions and 5' non-translated regions on the expression of genes in plant cells. It may be possible to increase the expression of a gene in a plant cell by means of such modifications. Such modifications, if performed upon chimeric genes of this invention, are within the scope of this invention.

Figure 3:
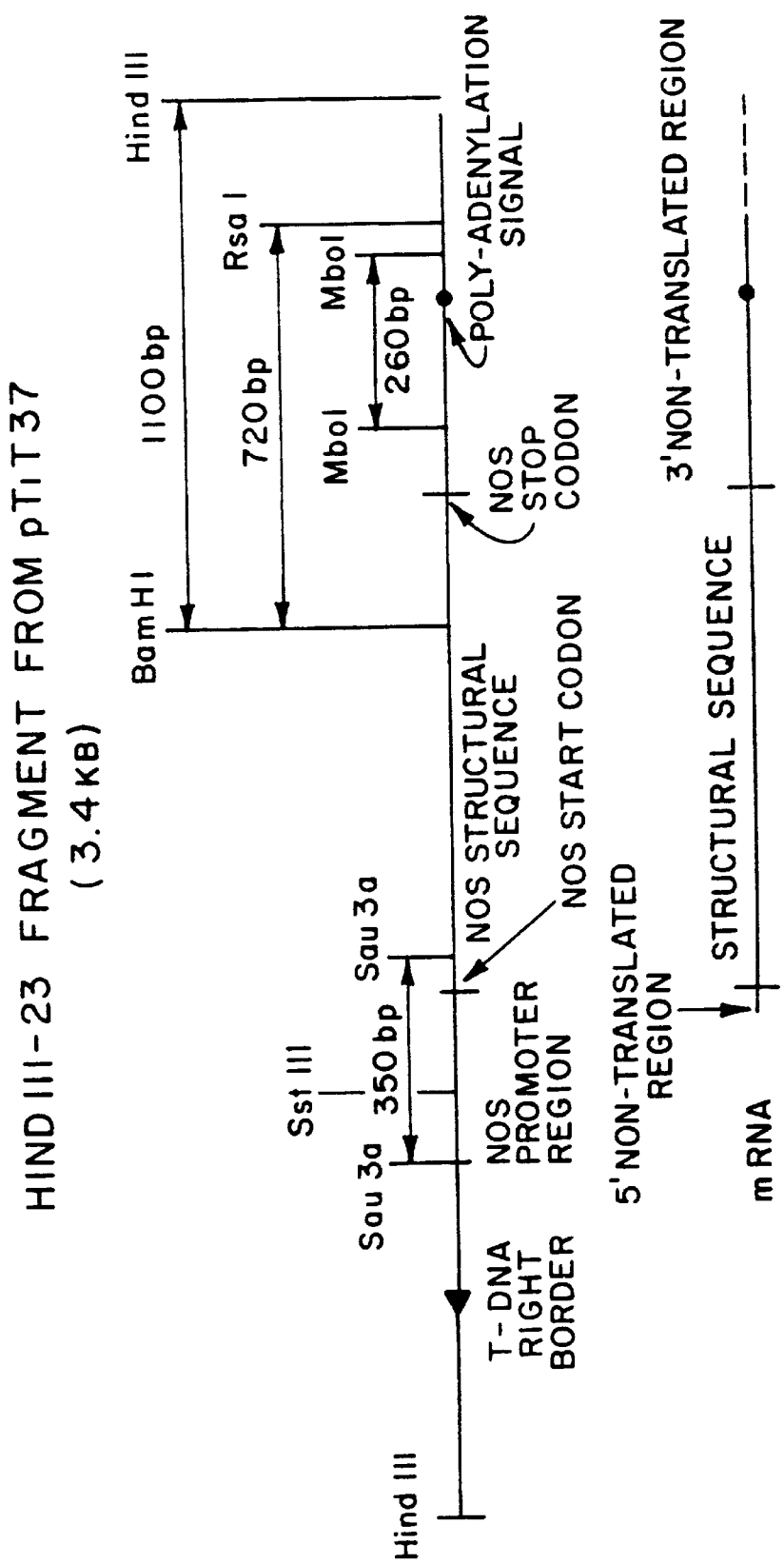
FIG. 3 represents fragment HindIII-23, obtained by digesting a Ti plasmid with HindIII.

A nopaline-type tumor-inducing plasmid, designated as pTiT37, was isolated from a strain of *A. tumefaciens* using standard procedures (Currier and Nester, 1976). It was digested with the endonuclease HindIII which produced numerous fragments. These fragments were separated by size on a gel, and one of the fragments was isolated and removed from the gel. This fragment was designated as the HindIII-23 fragment, because it was approximately the 23rd largest fragment from the Ti plasmid; it is approximately 3400 base pairs (bp) in size, also referred to as 3.4 kilobases (kb). From work by others (see, e.g., Hernalsteens et al., 1980), it was known that the HindIII-23 fragment contained the entire NOS gene, including the promoter region, a 5' non-translated region, a structural sequence with a start codon and a stop codon, and a 3' non-translated region. The HindIII-23 fragment is shown in FIG. 3.

By means of various cleavage and sequencing experiments, it was determined that the HindIII-23 fragment could be digested by another endonuclease, Sau3a, to yield a fragment, about 350 bp in size, which contains the entire NOS promoter region, the 5' non-translated region, and the first few codons of the NOS structural sequence. This fragment was sequenced, and the base sequence is represented in FIG. 4. The start codon (ATG) of the NOS structural sequence begins at base pair 301 within the 350 bp fragment. The Applicants decided to cleave the fragment between base pairs 300 and 301; this would provide them with a fragment about 300 base pairs long containing a NOS promoter region and the entire 5' non-translated region but with no translated bases. To cleave the 350 bp fragment at precisely the right location, the Applicants obtained an M13 clone designated as S1A, and utilized the procedure described below.

To create the S1A clone, Dr. Michael Bevan of Washington University converted the 350 bp Sau3a fragment into a single strand of DNA. This was done by utilizing a virus vector, designated as the M13 mp2 phage, which goes through both double-stranded (ds) and single-stranded (ss) stages in its life cycle (Messing et al., lg81). The ds 350 bp fragment was inserted into the double-stranded replicative form DNA of the M13 mp2, which had been cleaved with BamHI. The two fragments were ligated, and used to infect *E. coli* cells. The ds DNA containing the 350 bp inserted fragment subsequently replicated, and one strand (the viral strand) was encapsulated by the M13 viral capsid proteins. In one clone, designated the S1A, the orientation of the 350 bp fragment was such that the anti-sense strand (containing the same sequence as the mRNA) of the NOS gene was carried in the viral strand. Viral particles released from infected cells were isolated, and provided to the Applicants.

Single stranded S1A DNA, containing the anti-sense 350 bp fragment with the NOS promoter region, was isolated from the viral particles and sequenced. A 14-mer oligonucleotide primer was synthesized, using published procedures (Beaucage and Carruthers, 1981, as modified by Adams et al., 1982). This 14-mer was designed to be complementary to bases 287 through 300 of the 350 bp fragment, as shown on FIG. 4.

The 5' end of the synthetic primer was radioactively labelled with $^{32}P$; this is represented in the figures by an asterisk.

Figure 5:
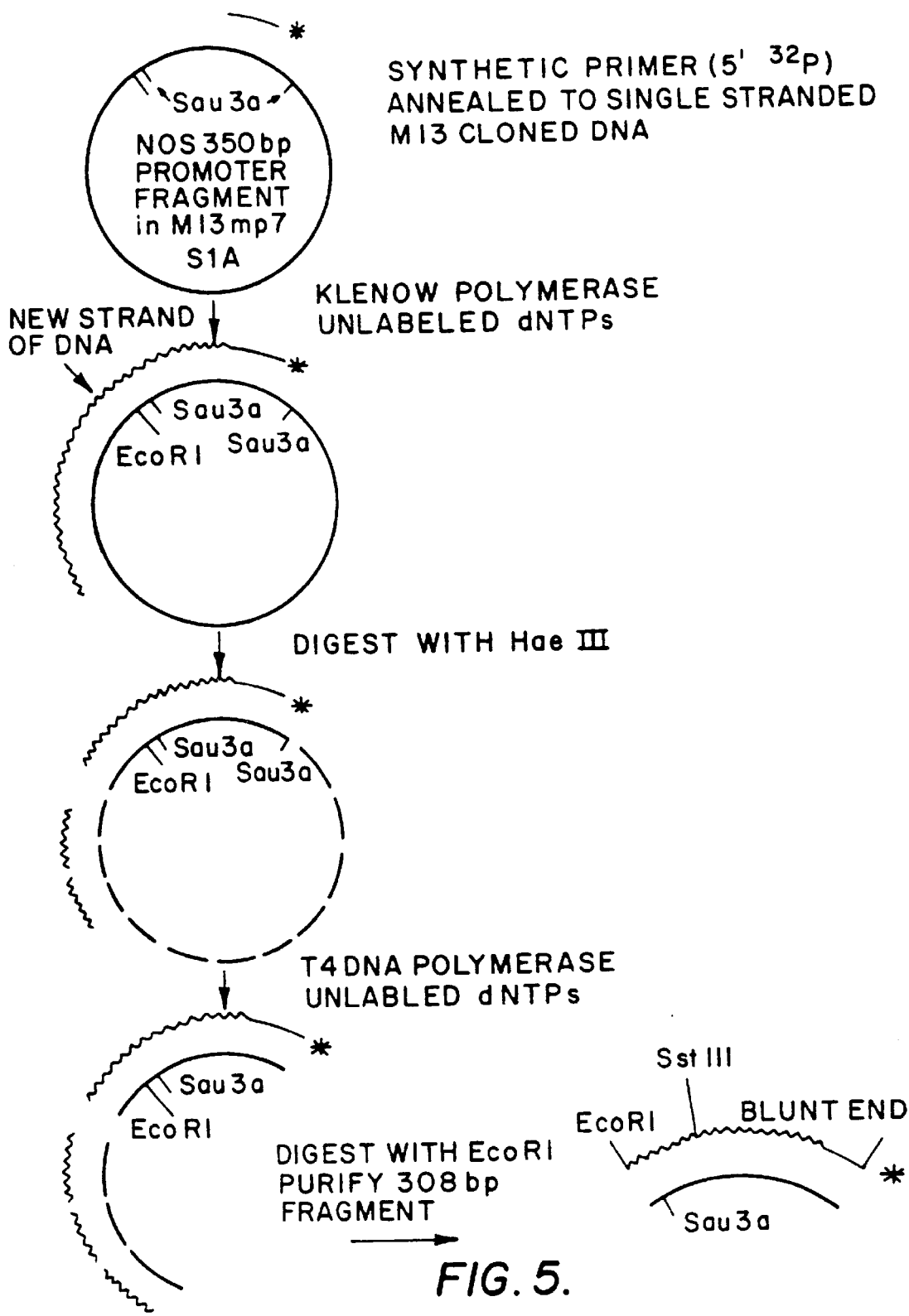
FIG. 5 represents the cleavage of a DNA sequence at a precise location, to obtain a DNA fragment which contains a NOS promoter region and complete 5' non-translated region.

Copies of the primer were mixed with copies of the single-stranded S1A DNA containing the anti-sense strand of the 350 bp fragment. The primer annealed to the desired region of the S1A DNA, as shown at the top of FIG. 5. After this occurred, Klenow DNA polymerase and a controlled quantity of unlabelled deoxynucleoside triphosphates (dNTP's), A, T, C, and G, were added. Klenow polymerase added nucleotides to the 3' (unlabelled) end of the primer, but not to the 5' (labelled) end. The result, as shown in FIG. 5, was a circular loop of single-stranded DNA, part of which was matched by a second strand of DNA. The 5' end of the second strand was located opposite base #300 of the Sau3a insert.

The partially double-stranded DNA was then digested by a third endonuclease, HaeIII, which can cleave both single-stranded and double-stranded DNA. HaeIII cleavage sites were known to exist in several locations outside the 350 bp insert, but none existed inside the 350 bp insert. This created a fragment having one blunt end, and one 3' overhang which started at base #301 of the Sau3a insert.

The HaeIII fragment mixture was treated with T4 DNA polymerase and unlabelled dNTP's. This caused the single stranded portion of the DNA, which extended from base #301 of the Sau3a insert to the closest HaeIII cleavage site, to be removed from the fragment. In this manner, the ATG start codon was removed from base pair #300, leaving a blunt end double-stranded fragment which was approximately 550 bp long.

The mixture was then digested by a fourth endonuclease EcoRI, which cleaved the 550 bp fragment at a single site outside the NOS promoter region. The fragments were then separated by size on a gel, and the radioactively-labelled fragment was isolated. This fragment contained the entire NOS promoter region and 5' non-translated region. It had one blunt end with a sequence of

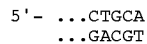

and one cohesive end (at the EcoRI site) with a sequence of

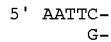

The shorter strand was about 308 bp long.

The foregoing steps are represented in FIG. 2 as steps 42, 44, and 46.

Figure 7:
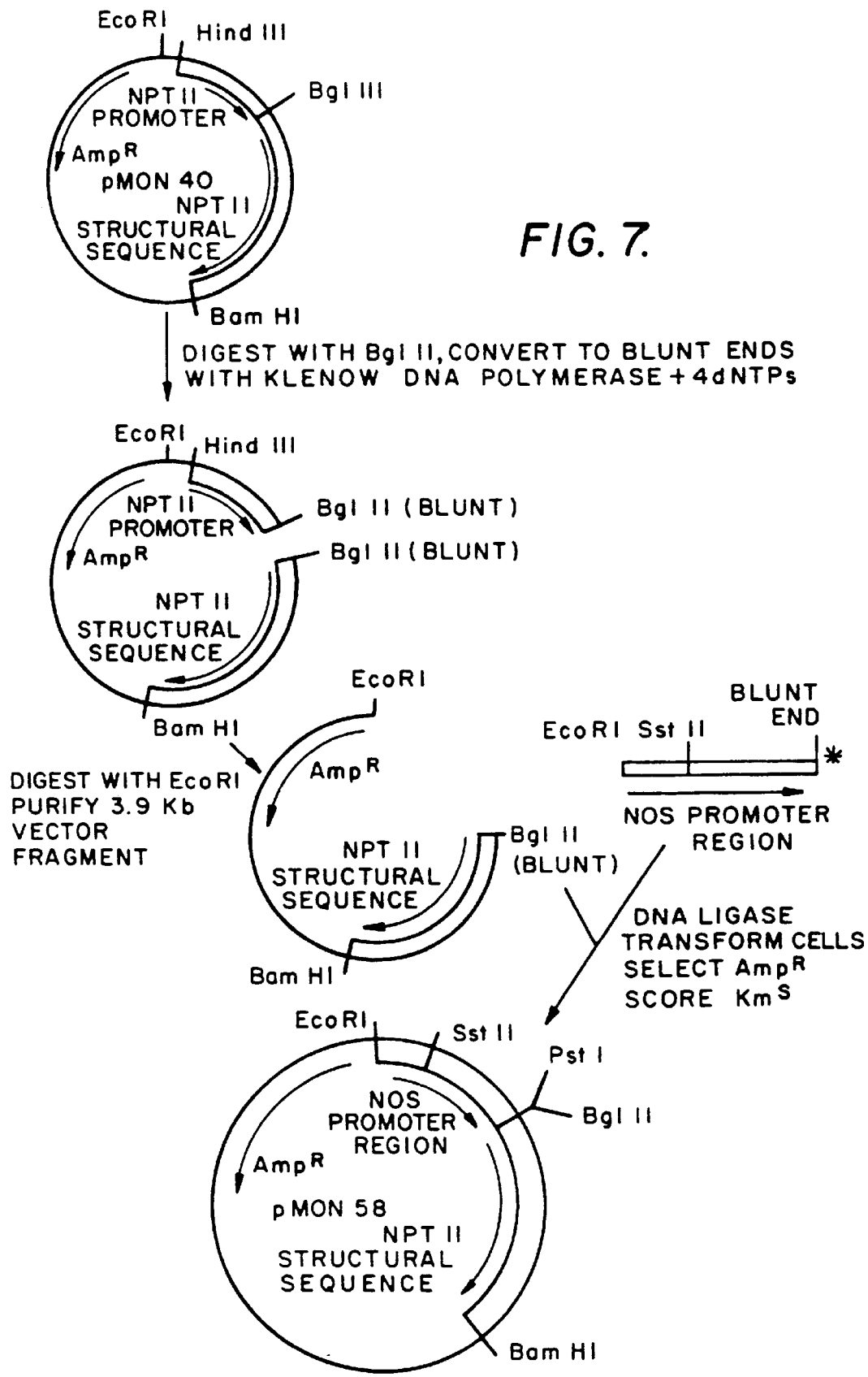
FIG. 7 represents the insertion of a NOS promoter region into plasmid pMON40, to obtain pMON58.

This fragment was inserted into pMON40 (which is described below) to obtain pMON58, as shown on FIG. 7.

Creation of Plasmid with NPTII Gene (pMON40)

Figure 6:
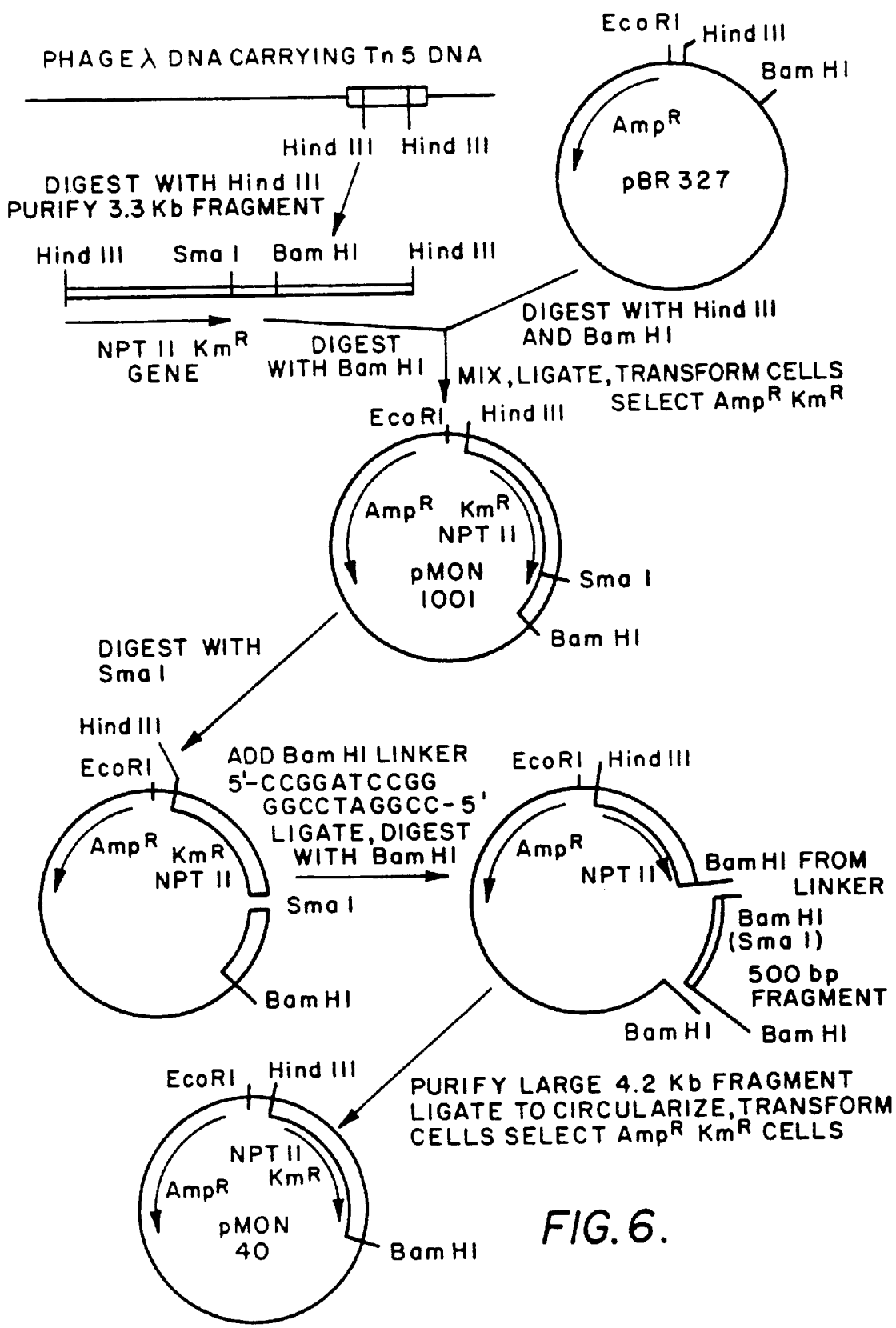
FIG. 6 represents the creation of plasmids pMON1001 and pMON40, which contain an NPTII structural sequence.

A bacterial transposon, designated as Tn5, is known to contain a complete NPTII gene, including promoter region, structural sequence, and 3' non-translated region. The NPTII enzyme inactivates certain aminoglycoside antibiotics, such as kanamycin, neomycin, and G418; see Jimenez and Davies, 1980. This gene is contained within a 1.8 kb fragment, which can be obtained by digesting phage lambda bbkan-1 DNA (D. Berg et al., 1975) with two endonucleases, HindII and BamHI. This fragment was inserted into a common laboratory plasmid, pBR327, which had been digested by HindIII and BamHI. As shown in FIG. 6, the resulting plasmid was designated as pMON1001, which was about 4.7 kb.

To reduce the size of the DNA fragment which carried the NPTII structural sequence, the Applicants eliminated about 500 bp from the pMON1001 plasmid, in the following manner. First, they digested pMON1001 at a unique SmaI restriction site which was outside of the NPTII gene. Next, they inserted a 10-mer synthetic oligonucleotide linker,

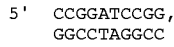

into the SmaI cleavage site. This eliminated the SmaI cleavage site and replaced it with a BamHI cleavage site. A second BamHI cleavage site already existed, about 500 bp from the new BamHI site. The Applicants digested the plasmid with BamHI, separated the 500 bp fragment from the 4.2 kb fragment, and circularized the 4.2 kb fragment. The resulting plasmids were inserted into *E. coli*, which were then selected for resistance to ampicillin and kanamycin. A clonal colony of *E. coli* was selected; these cells contained a plasmid which was designated as pMON40, as shown in FIG. 6.

The foregoing steps are represented in FIG. 2 as steps 48 and 50.

Insertion of NOS Promoter into Plasmid pMON40

The Applicants deleted the NPTII promoter from pMON40, and replaced it with the NOS promoter fragment described previously, by the following method, shown on FIG. 7.

Previous cleavage and sequencing experiments (Rao and Rogers, 1979; Auerswald et al., 1980) indicated that a BglII cleavage site existed in the NPTII gene between the promoter region and the structural sequence. Plasmid pMON40 was digested with BglII. The cohesive ends were then filled in by mixing the cleaved plasmid with Klenow polymerase and the four dNTP's, to obtain the following blunt ends:

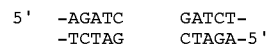

The polymerase and dNTP's were removed, and the cleaved plasmid was then digested with EcoRI. The smaller fragment which contained the NPTII promoter region was removed, leaving a large fragment with one EcoRI end and one blunt end. This large fragment was mixed with the 308 bp fragment which contained the NOS promoter, described previously and shown on FIG. 5. The fragments were ligated, and inserted into *E. coli*. *E coli* clones were selected for ampicillin resistance. Replacement of the NPTII promoter region (a bacterial promoter) with the NOS promoter region (which is believed to be active only in plant cells) caused the NPTII structural sequence to become inactive in *E. coli*. Plasmids from 36 kanamycin-sensitive clones were obtained; the plasmid from one clone, designated as pMON58, was utilized in subsequent work.

The foregoing steps are represented in FIG. 2 as steps 52 and 54.

Plasmid pMON58 may be digested to obtain a 1.3 kb EcoRI-BamHI fragment which contains the NOS promoter region, the NOS 5' non-translated region, and the NPTII structural sequence. This step is represented in FIG. 2 as step 56.

Insertion of NOS 3' Sequence into NPTII Gene

As mentioned above in "Background Art," the functions of 3' non-translated regions in eucaryotic genes are not fully understood. However, they are believed to contain at least one important sequence, a poly-adenylation signal.

It was suspected by the Applicants that a gene having a bacterial 3' non-translated region might not be expressed as effectively in a plant cell as the same gene having a 3' non-translated region from a gene, such as NOS, which is known to be expressed in plants. Therefore, the Applicants decided to add a NOS 3' non-translated region to the chimeric gene, in addition to the NPTII 3' non-translated region already present. Whether a different type of 3' non-translated region (such as a 3' region from an octopine-type or agropine-type Ti plasmid, or a 3' region from a gene that normally exists in a plant cell) would be suitable or preferable for use in any particular type of chimeric gene, for use in any specific type of plant cell, may be determined by those skilled in the art through routine experimentation using the method of this invention. Alternately, it is possible, using the methods described herein, to delete the NPTII or other existing 3' non-translated region and replace it with a desired 3' non-translated region that is known to be expressed in plant cells.

Those skilled in the art may also determine through routine experimentation whether the 3' non-translated region that naturally follows a structural sequence that is to be inserted into a plant cell will enhance the efficient expression of that structural sequence in that type of plant cell. If so, then the steps required to insert a different 3' non-translated region into the chimeric gene might not be required in order to perform the method of this invention.

In order to obtain a DNA fragment containing a NOS 3' non-translated region appropriate for joining to the NPTII structural sequence from pMON58 (described previously), the Applicants utilized a 3.4 kb HindIII-23 fragment from a Ti plasmid, shown on FIG. 3. This 3.4 kb fragment was isolated and digested with BamHI to obtain a 1.1 kb BamHI-HindiIII fragment containing a 3' portion of the NOS structural sequence (including the stop codon), and the 3' non-translated region of the NOS gene (including the poly-adenylation signal). This 1.1 kb fragment was inserted into a pBR327 plasmid which had been digested with HindIII and BamHI. The resulting plasmid was designated as pMON42, as shown on FIG. 8.

Plasmid pMON42 was digested with BamHI and RsaI, and a 720 bp fragment containing the desired NOS 3' non-translated region was purified on a gel. The 720 bp fragment was digested with another endonuclease, MboI, and treated with the large fragment of E. coli DNA polymerase I. This resulted in a 260 bp fragment with MboI blunt ends, containing a large part of the NOS 3' non-translated region including the poly-A signal.

The foregoing procedure is represented in FIG. 2 by step 58. However, it is recognized that alternate means could have been utilized; for example, it might have been possible to digest the HindIII-23 fragment directly with MboI to obtain the desired 260 bp fragment with the NOS 3' non-translated region.

Assembly of Chimeric Gene

To complete the assembly of the chimeric gene, it was necessary to ligate the 260 bp MboI fragment (which contained the NOS 3' non-translated region) to the 1.3 kb EcoRI-BamHI fragment from pMON58 (which contained the NOS promoter region and 5' non-translated region and the NPTII structural sequence). In order to facilitate this ligation and control the orientation of the fragments, the Applicants decided to convert the MboI ends of the 260 bp fragment into a BamHI end (at the 5' end of the fragment) and an EcoRI end (at the 3' end of the fragment). In order to perform this step, the Applicants used the following method.

Figure 8:
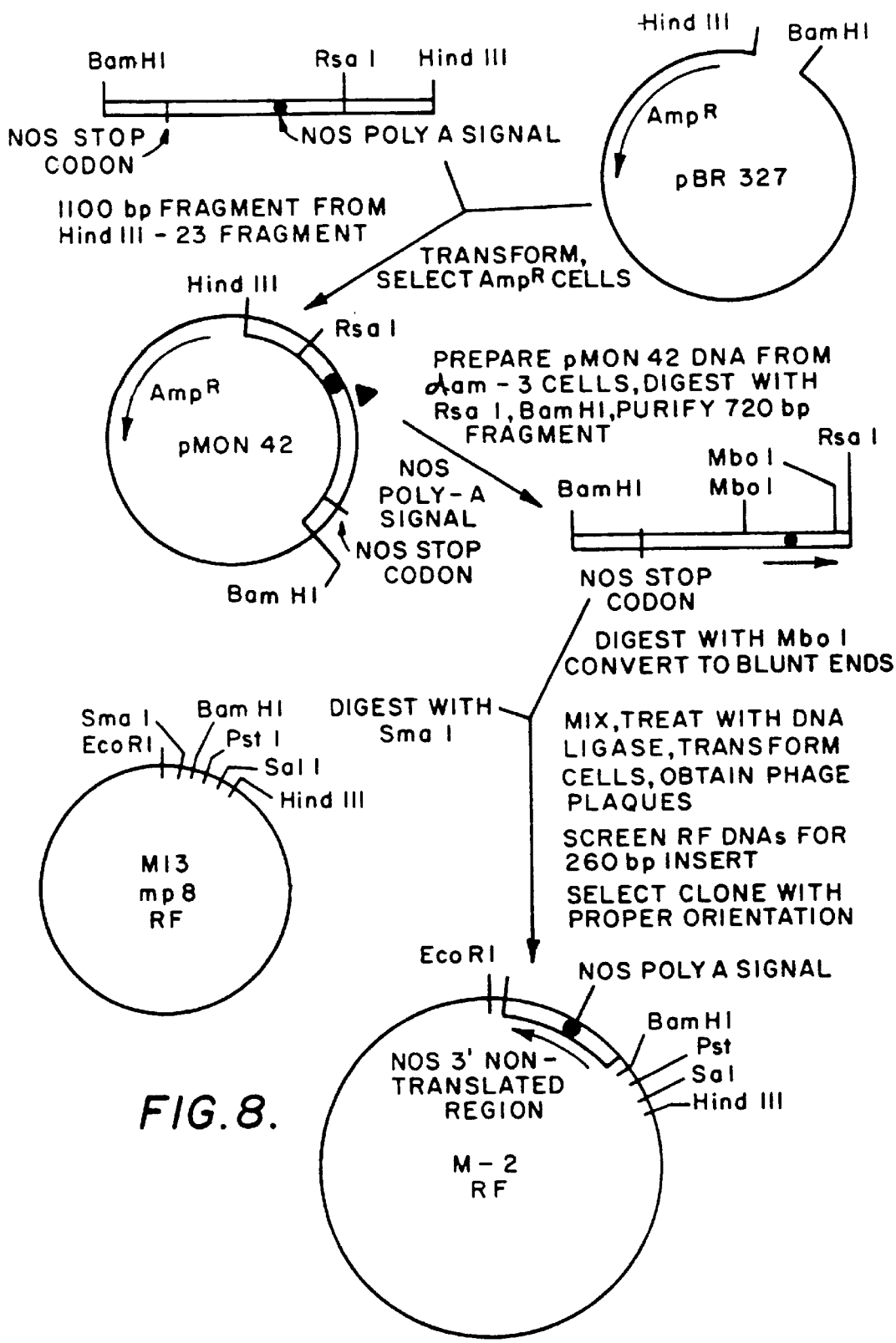
FIG. 8 represents the creation of an M13 derivative designated as M-2, which contains a NOS 3' non-translated region and poly-A signal.

The 260 bp MboI fragment, the termini of which had been converted to blunt ends by Klenow polymerase, was inserted into M13 mp8 DNA at a SmaI cleavage site. The SmaI site is surrounded by a variety of other cleavage sites present in the M13 mp8 DNA, as shown in FIG. 8. The MboI fragment could be inserted into the blunt SmaI ends in either orientation. The orientation of the MboI fragments in different clones were tested, using HinfI cleavage sites located asymmetrically within the MboI fragment. A clone was selected in which the 3' end of the NOS 3' non-translated region was located near the EcoRI cleavage site in the M13 mp8 DNA. This clone was designated as the M-2 clone, as shown in FIG. 8.

Figure 9:
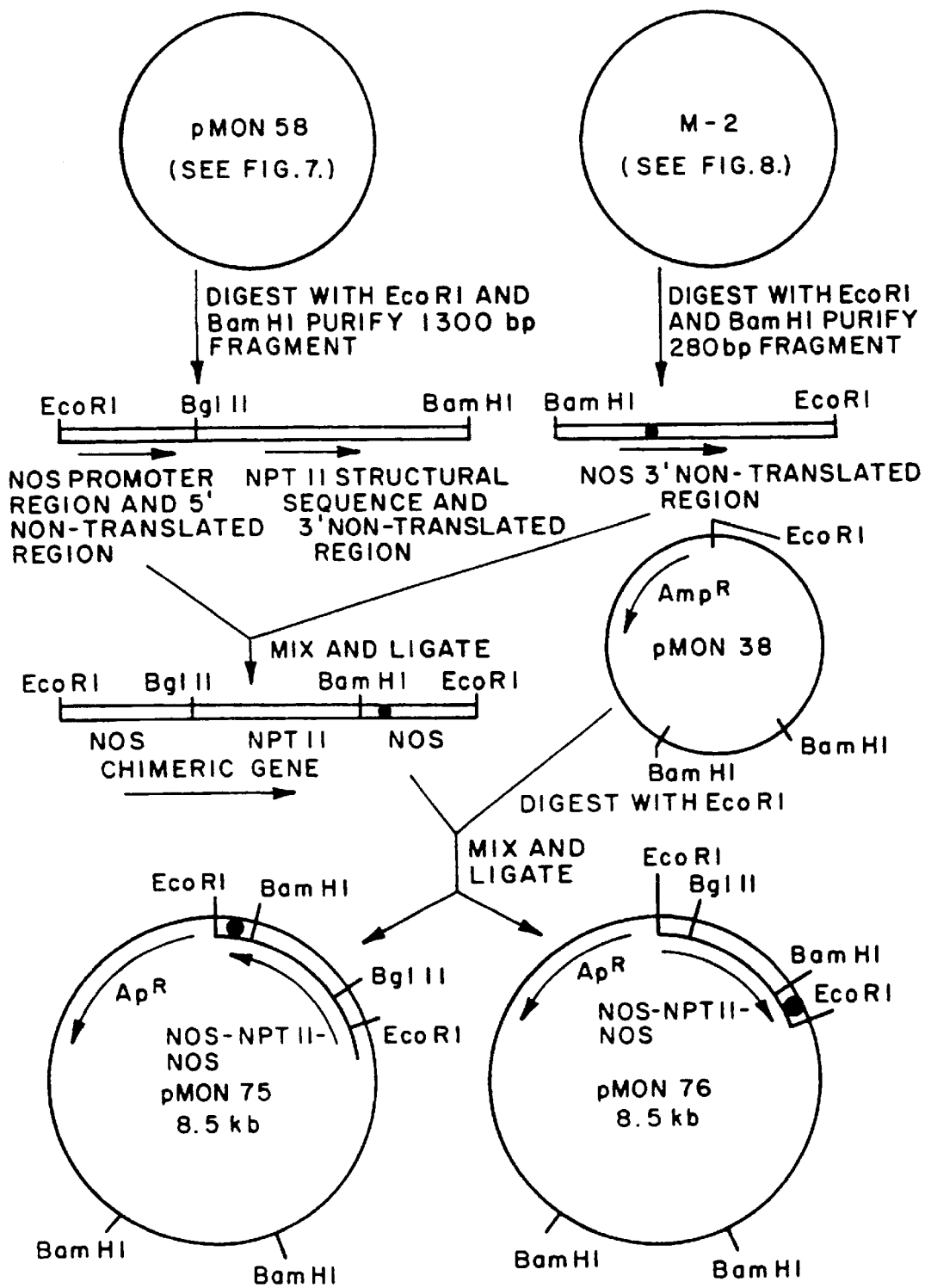
FIG. 9 represents the assembly of the NOS-NPTII-NOS chimeric gene, and the insertion of the chimeric gene into plasmid pMON38 to obtain plasmids pMON75 and pMON76.

Replicative form (double stranded) DNA from the M-2 clone was digested by EcoRI and BamHI and a 280 bp fragment was isolated. Separately, plasmid pMON58 was digested by EcoRI and BamHI, and a 1300 bp fragment was isolated. The two fragments were ligated, as shown in FIG. 9, to complete the assembly of a NOS-NPTII-NOS chimeric gene having EcoRI ends.

There are a variety of ways to control the ligation of the two fragments. For example, the two EcoRI-BamHI fragments could be joined together with DNA ligase and cleaved with EcoRI. After inactivation of EcoRI, a vector molecule having EcoRI ends that were treated with calf alkaline phosphatase (CAP) may be added to the mixture. The fragments in the mixture may be ligated in a variety of orientations. The plasmid mixture is used to transform E. coli, and cells having plasmids with the desired orientation are selected or screened, as described below.

A plasmid, designated as pMON38, was created by insertion of the HindIII-23 fragment (from Ti plasmid pTiT37) into the HindIII cleavage site of the plasmid pBR327. Plasmid pMON38 contains a unique EcoRI site, and an ampicillin-resistance gene which is expressed in E. coli. Plasmid pMON38 was cleaved with EcoRI and treated with alkaline phosphatase to prevent it from re-ligating to itself. U.S. Pat. No. 4,264,731 (Shine, 1981). The resulting fragment was mixed with the 1300 bp NOS-NPTII fragment from pMON58, and the 280 bp NOS fragment from M-2, which had been ligated and EcoRI-cleaved as described in the previous paragraph. The fragments were ligated, and inserted into E. coli. The E. coli cells which had acquired intact plasmids with ampicillin-resistance genes were selected on plates containing ampicillin. Several clones were selected, and the orientation of the inserted chimeric genes was evaluated by means of cleavage experiments. Two clones having plasmids carrying NOS-NPTII-NOS inserts with opposite orientations were selected and designated as pMON75 and pMON76, as shown in FIG. 9. The chimeric gene may be isolated by digesting either pMON75 or pMON76 with EcoRI and purifying a 1580 bp fragment.

The foregoing procedure is represented on FIG. 2 by step 60.

This completes the discussion of the NOS-NPTII-NOS chimeric gene. Additional information on the creation of this gene is provided in the Examples. A copy of this chimeric gene is contained in plasmid pMON128; it may be removed from pMON128 by digestion with EcoRI. A culture of E. coli containing pMON128 has been deposited with the American Type Culture Collection; this culture -has been assigned accession number 39264.

To prove the utility of this chimeric gene, the Applicants inserted it into plant cells. The NPTII structural sequence was expressed in the plant cells, causing them and their descendants to acquire resistance to concentrations of kanamycin which are normally toxic to plant cells.

In an alternate preferred embodiment of this invention, a chimeric gene was created comprising (1) a NOS promoter region and 5' non-translated region, (2) a structural sequence which codes for NPT I, and (3) a NOS 3' non-translated region. NPTI and NPTII are different and distinct enzymes with major differences in their amino acid sequences and substrate specificities. See, e.g., E. Beck et al., 1982. The relative stabilities and activities of these two enzymes in various types of plant cells are not yet fully understood, and NPTI may be preferable to NPTII for use in certain types of experiments and plant transformations.

Figure 11:
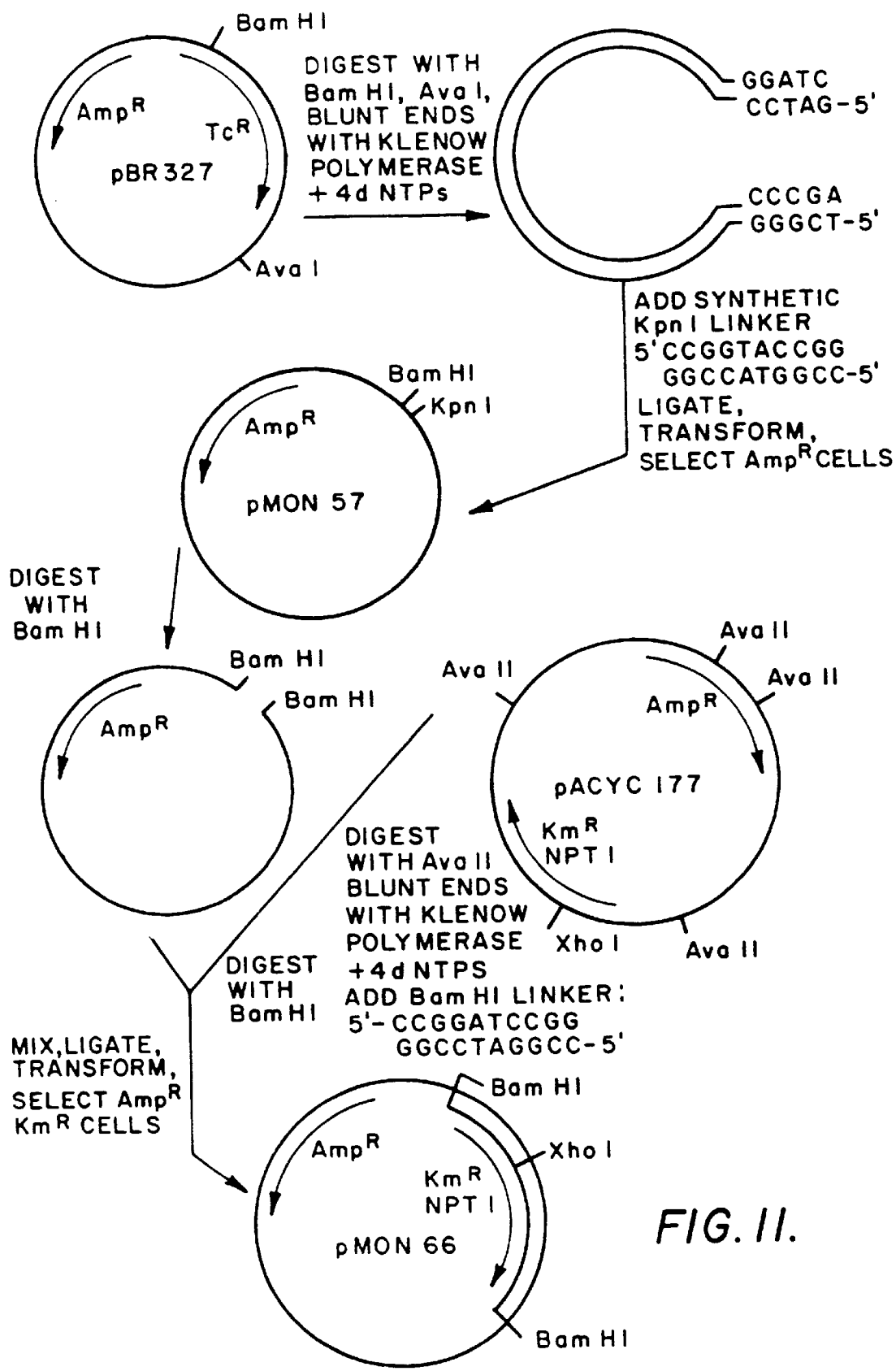
FIG. 11 represents the creation of plasmid pMON66, which contains an NPTI gene.

A 1200 bp fragment containing an entire NPTI gene was obtained by digesting pACYC177 (Chang and Cohen, 1978) with the endonuclease, AvaII. The AvaII termini were converted to blunt ends with Klenow polymerase, and converted to BamHI termini using a synthetic linker. This fragment was inserted into a unique BamHI site in a pBR327-derived plasmid, as shown in FIG. 11. The resulting plasmid was designated as pMON66.

Plasmid pMON57 (a deletion derivative of pBR327, as shown in FIG. 11) was digested with AvaII. The 225 bp fragment of pMON57 was replaced by the analogous 225 bp AvaII fragment taken from plasmid pUC8 (Vieira and Messing, 1982), to obtain a derivative of pMON57 with no PstI cleavage sites. This plasmid was designated as pMON67.

Plasmid pMON58 (described previously and shown in FIG. 7) was digested with EcoRI and BamHI to obtain a 1300 bp fragment carrying the NOS promoter and the NPTII structural sequence.

Figure 12:
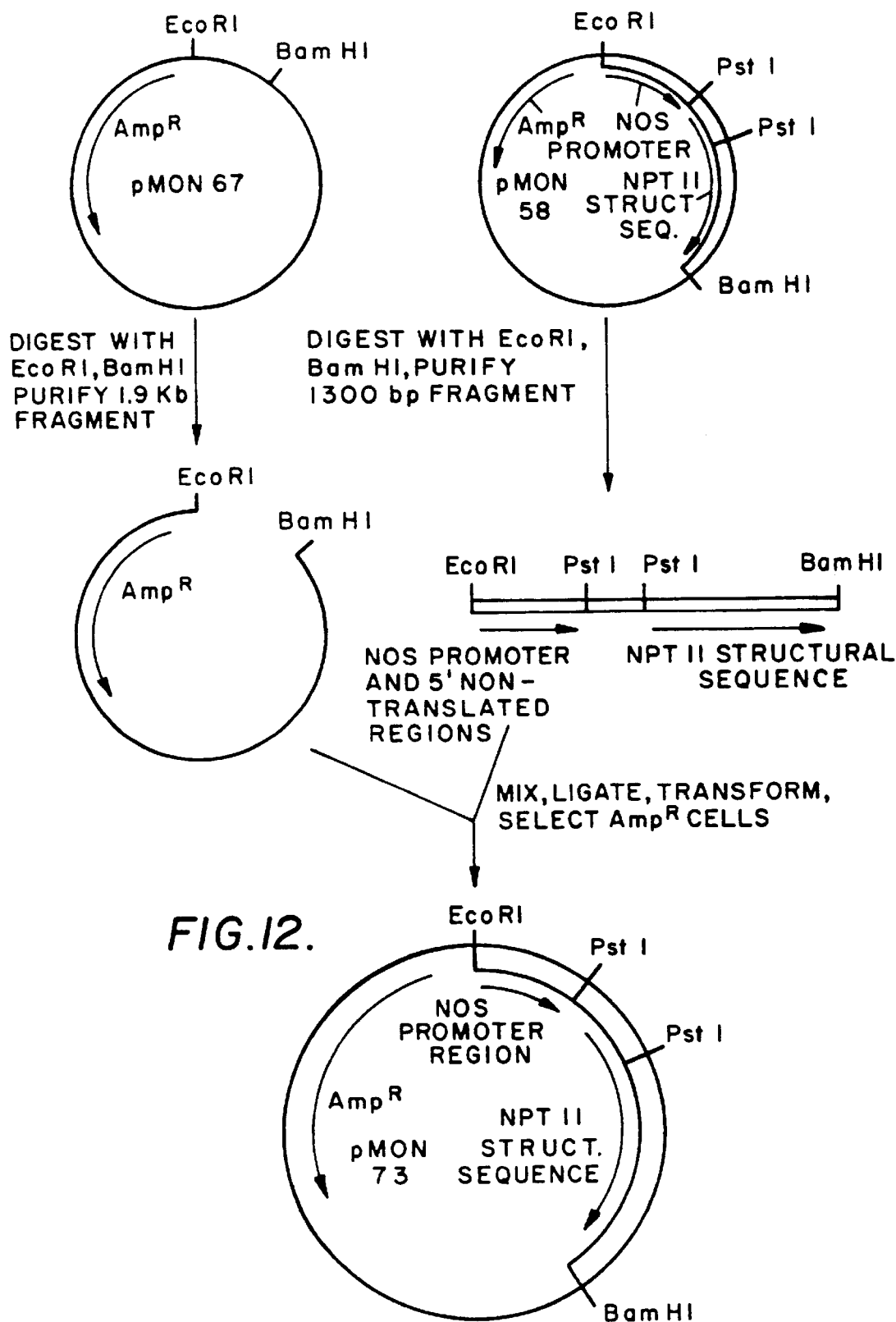
FIG. 12 represents the creation of plasmid pMON73, containing a chimeric NOS-NPTII sequence.
Figure 13:
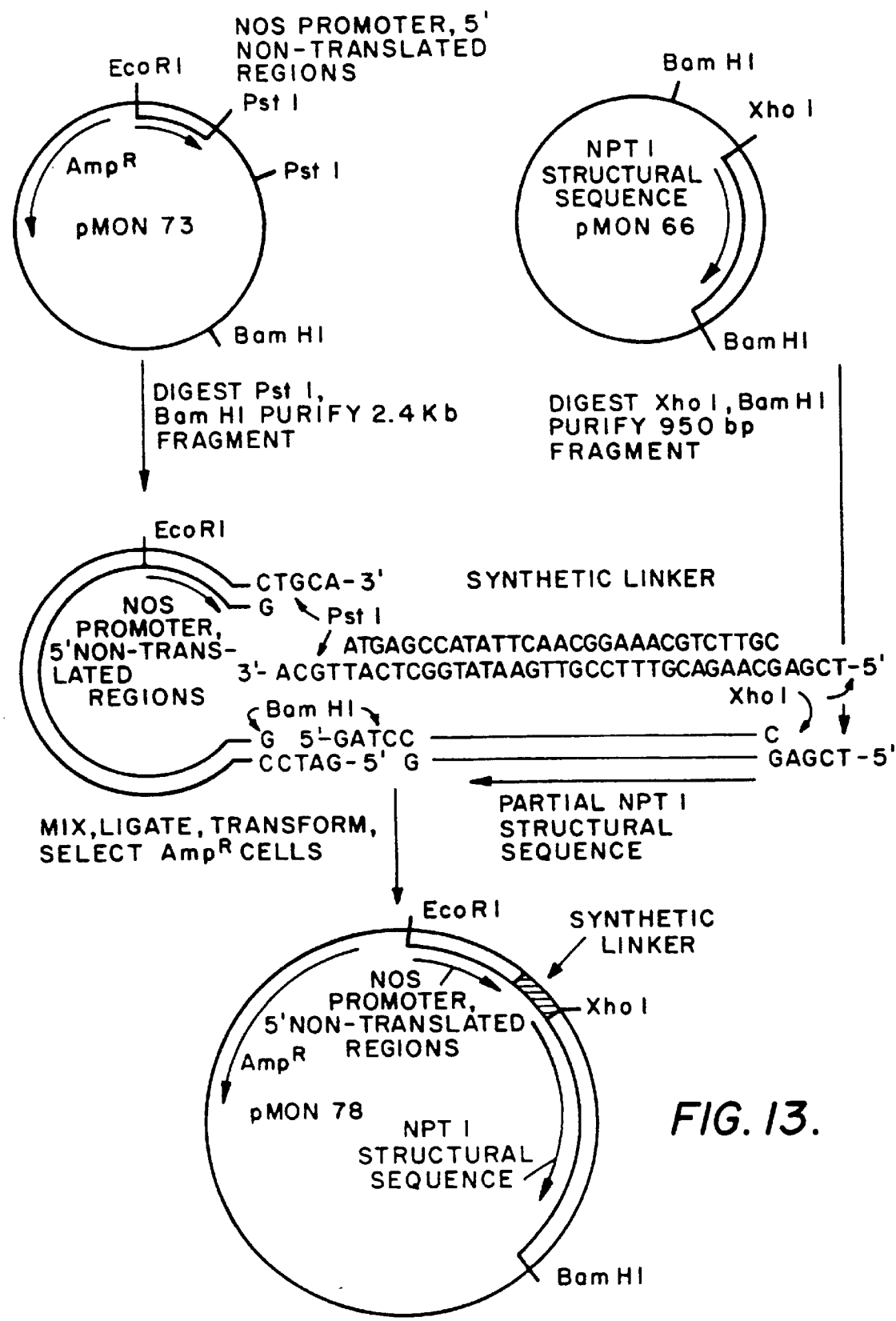
FIG. 13 represents the creation of plasmid pMON78, containing a chimeric NOS-NPTI sequence.

This fragment was inserted into pMON67 which had been digested with EcoRI and BamHI. The resulting plasmid was designated as pMON73, as shown in FIG. 12.

pMON73 was digested with PstI and BamHI, and a 2.4 kb fragment was isolated containing a NOS promoter region and 5' non-translated region. Plasmid pMON66 (shown on FIG. 11) was digested with XhoI and BamHI to yield a 950 bp fragment containing the structural sequence of NPTI. This fragment lacked about 30 nucleotides at the 5' end of the structural sequence. A synthetic linker containing the missing bases, having appropriate PstI and XhoI ends, was created. The pMON73 fragment, the pMON66 fragment, and the synthetic linker were ligated together to obtain plasmid pMON78, as shown in FIG. 13. This plasmid contains the NOS promoter region and 5' non-translated region adjoined to the NPTI structural sequence. The ATG start codon was in the same position that the ATG start codon of the NOS structural sequence had occupied.

Figure 14:
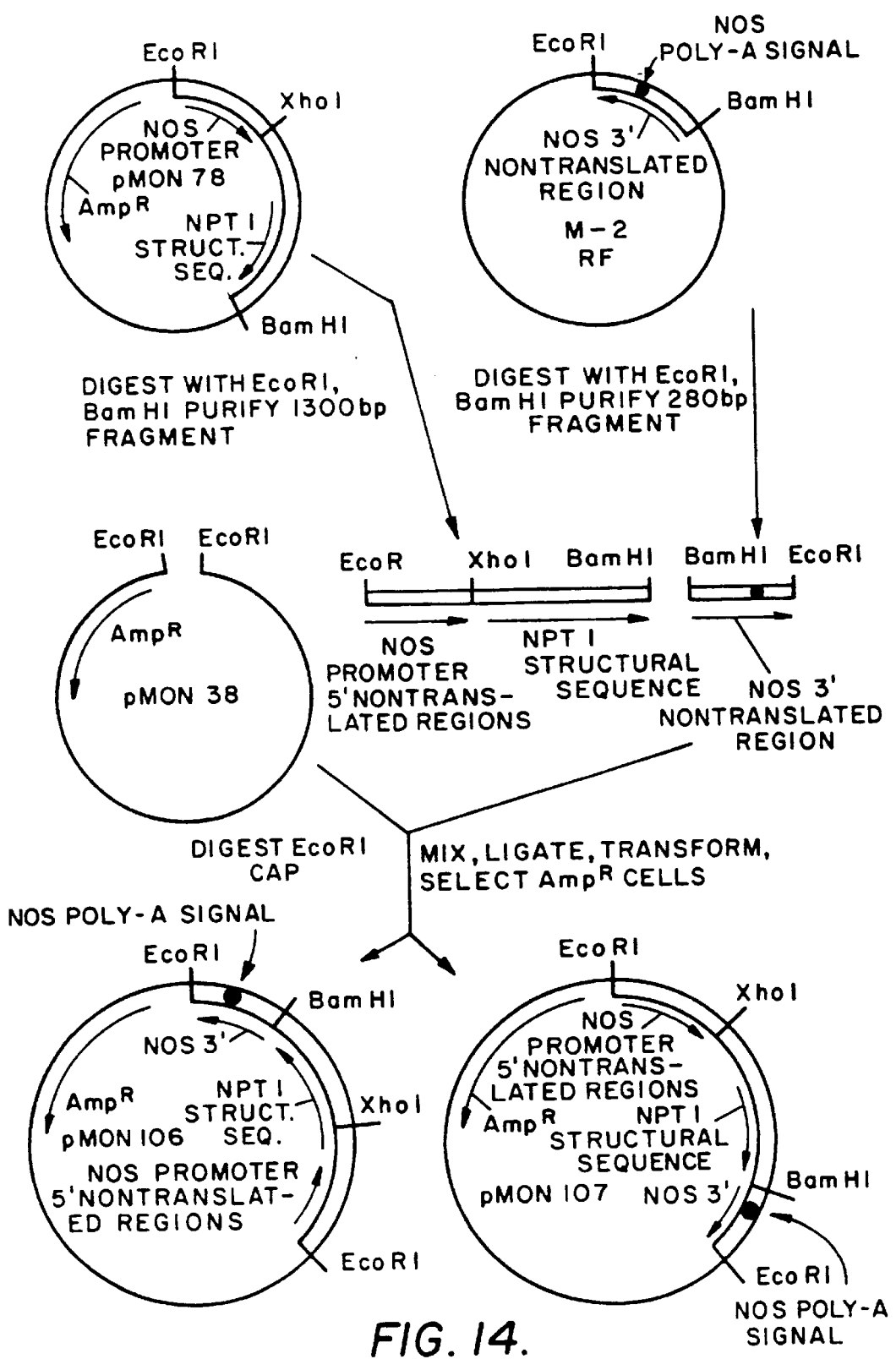
FIG. 14 represents the creation of plasmids pMON106 and pMON107, which contain chimeric NOS-NPTI-NOS genes.

Plasmid pMON78 was digested with EcoRI and BamHI to yield a 1300 bp fragment carrying the chimeric NOS-NPTI regions. Double-stranded DNA from the M-2 clone (described previously and shown on FIG. 9) was digested with EcoRI and BamHI, to yield a 280 bp fragment carrying a NOS 3' non-translated region with a poly-adenylation signal. The two fragments described above were ligated together to create the NOS-NPTI-NOS chimeric gene, which was inserted into plasmid pMON38 (described above) which had been digested with EcoRI. The two resulting plasmids, having chimeric gene inserts with opposite orientations, were designated as pMON106 and pMON107, as shown in FIG. 14.

Figure 15:
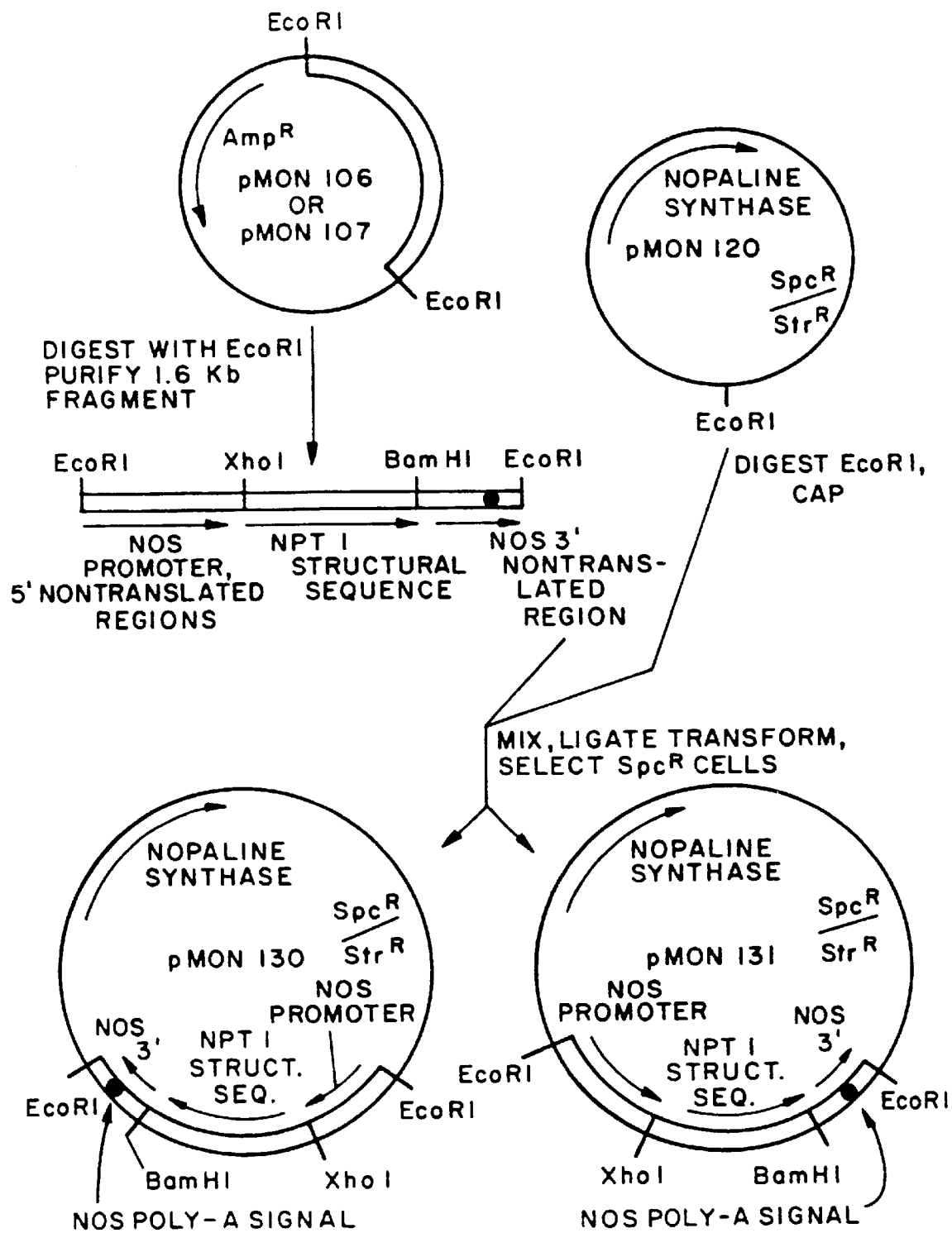
FIG. 15 represents the insertion of a chimeric NOS-NPTI-NOS gene into pMON120 to obtain plasmids pMON130 and pMON131.

Either of plasmids pMON106 or pMON107 may be digested with EcoRI to yield a 1.6 kb fragment containing the chimeric NOS-NPTI-NOS gene. This fragment was inserted into plasmid pMON120 which had been digested with EcoRI and treated with alkaline phosphatase. The resulting plasmids, having inserts with opposite orientations, were designated as pMON130 and pMON131, as shown on FIG. 15.

The NOS-NPTI-NOS chimeric gene was inserted into plant cells, which acquired resistance to kanamycin. This demonstrates expression of the chimeric gene in plant cells.

Creation of Chimeric Gene with Soybean Promoter

In an alternate preferred embodiment of this invention, a chimeric gene was created comprising (1) a promoter region and 5' non-translated region taken from a gene which naturally exists in soybean; this gene codes for the small subunit of ribulose-1,5-bisphosphate carboxylase (sbss for soybean small subunit); (2) a structural sequence which codes for NPTII, and (3) a NOS 3' non-translated region.

The sbss gene codes for a protein in soybean leaves which is involved in photosynthetic carbon fixation. The sbss protein is the most abundant protein in soybean leaves (accounting for about 10% of the total leaf protein), so it is likely that the sbss promoter region causes prolific transcription.

Figure 16:
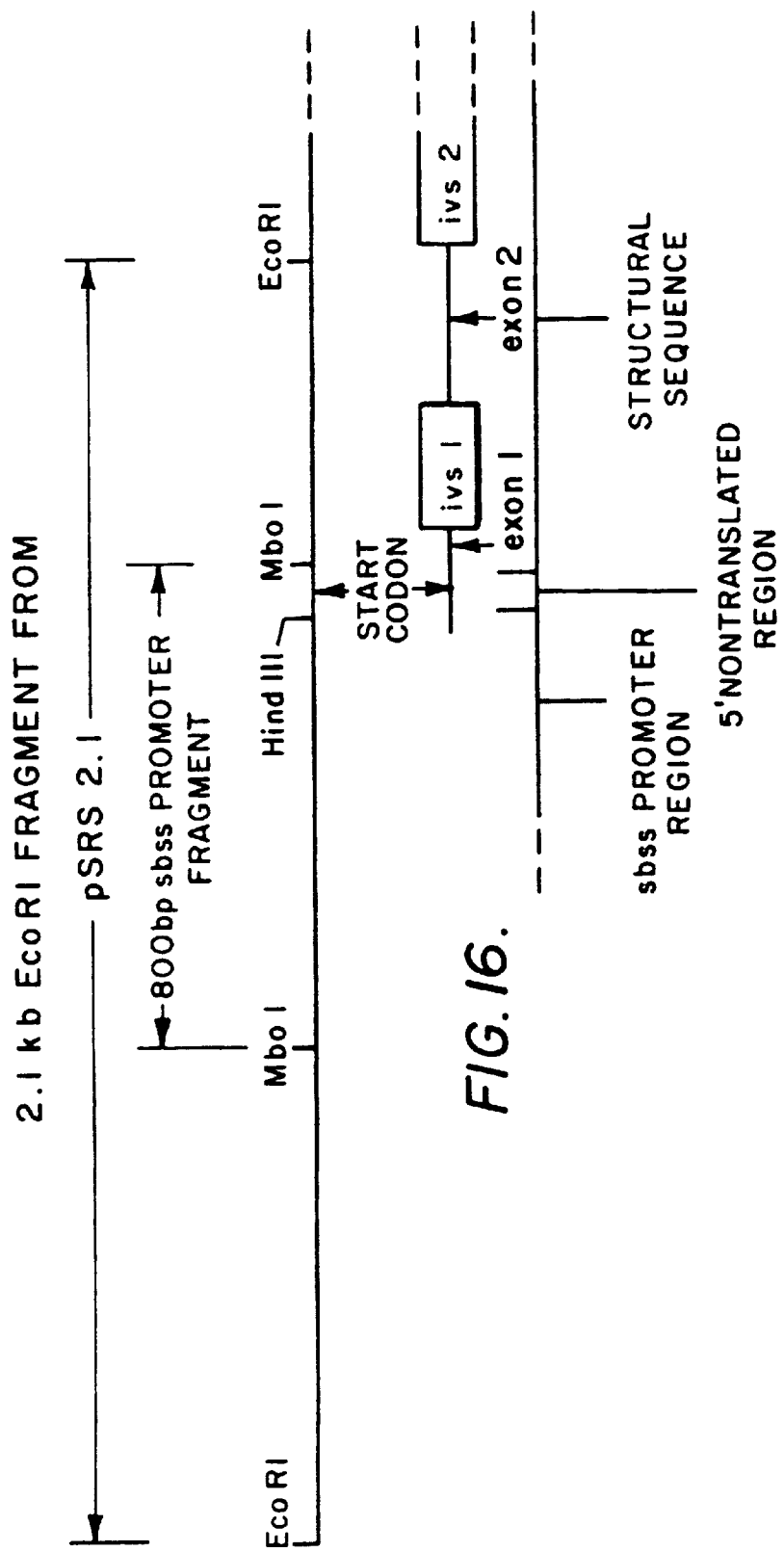
FIG. 16 represents the structure of a DNA fragment containing a soybean protein (sbss) promoter.

There are believed to be approximately six genes encoding the ss RuBPCase protein in the soybean genome. One of the members of the ss RuBPCase gene family, SRS1, which is highly transcribed in soybean leaves, has been cloned and characterized. The promoter region, 5' non-translated region, and a portion of the structural sequence are contained on a 2.1 kb EcoRI fragment that was subcloned into the EcoRI site of plasmid pBR325 (Bolivar, 1978). The resultant plasmid, pSRS2.1, was a gift to Monsanto Company from Dr. R. B. Meagher, University of Georgia, Athens, Ga. The 2.1 kb EcoRI fragment from pSRS2.1 is shown on FIG. 16.

Figure 17:
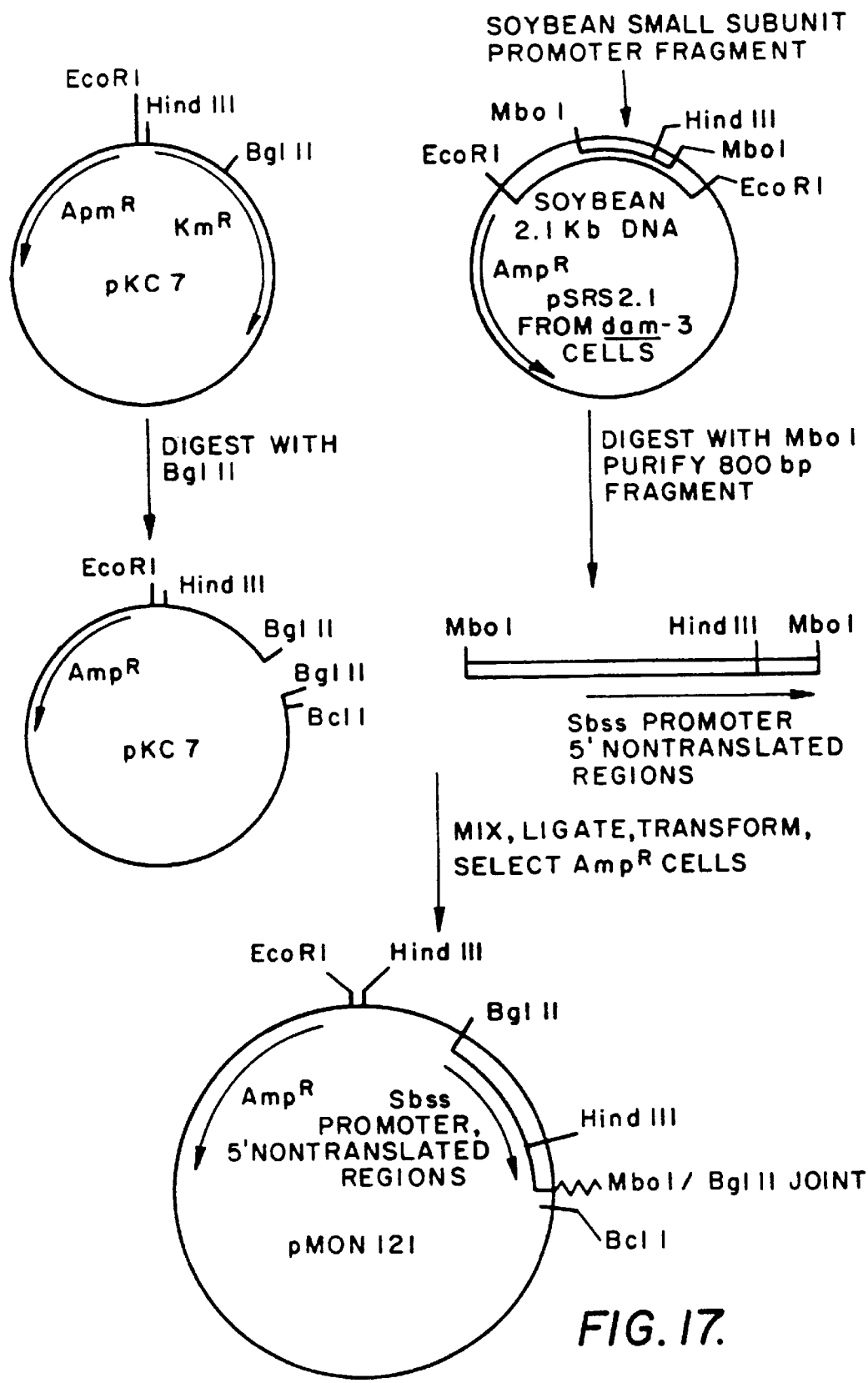
FIG. 17 represents the creation of plasmid pMON121, containing the sbss promoter.

Plasmid pSRS2.1 was prepared from dam⁻ E. coli cells, and cleaved with MboI to obtain an 800 bp fragment. This fragment was inserted into plasmid pKC7 (Rao and Rogers, 1979) which had been cleaved with BglII. The resulting plasmid was designated as pMON121, as shown on FIG. 17.

Figure 18:
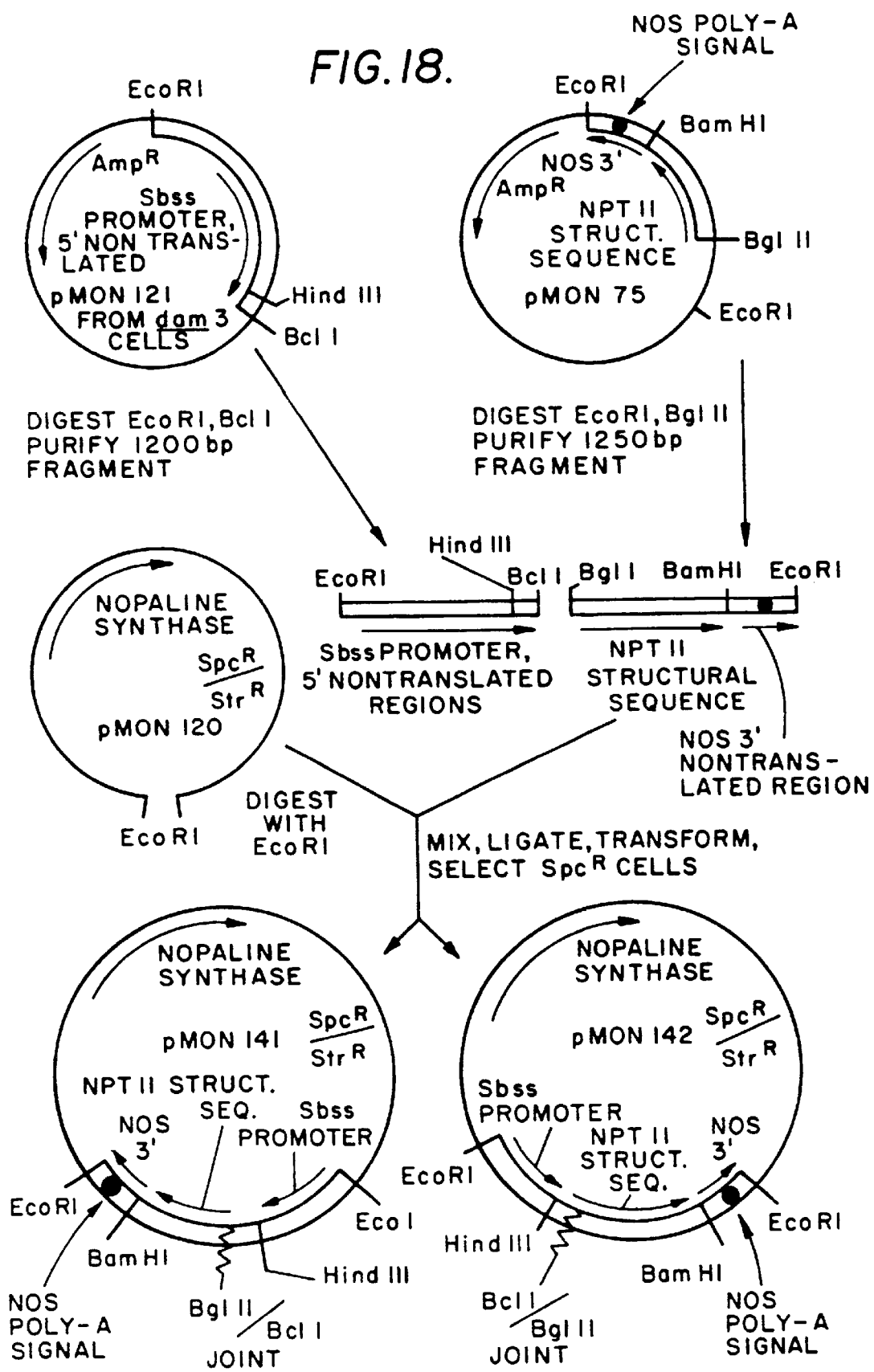
FIG. 18 represents the insertion of a chimeric sbss-NPTII-NOS gene into pMON120 to create plasmids pMON141 and pMON142.

Plasmid pMON121 was digested with EcoRI and BclI, and a 1200 bp fragment containing the sbss promoter region was isolated. Separately, plasmid pMON75 (described previously and shown on FIG. 9) was digested with EcoRI and BglII, and a 1250 bp fragment was isolated, containing a NPTII structural sequence and a NOS 3' non-translated region. The two fragments were ligated at the compatible BclI/BglII overhangs, to create a 2450 bp fragment containing sbss-NPTII-NOS chimeric gene. This fragment was inserted into pMON120 which had been cleaved with EcoRI, to create two plasmids having chimeric gene inserts with opposite orientations, as shown in FIG. 18. The plasmids were designated as pMON141 and pMON142.

The sbss-NPTII-NOS chimeric genes were inserted into several types of plant cells, causing the plant cells to acquire resistance to kanamycin.

This successful transformation proved that a promoter region from one type of plant can cause the expression of a gene within plant cells from an entirely different genus, family, and order of plants.

The chimeric sbss-NPTII-NOS gene also had another significant feature. Sequencing experiments indicated that the 800 bp MboI fragment contained the ATG start codon of the sbss structural sequence. Rather than remove this start codon, the Applicants decided to insert a stop codon behind it in the same reading frame.

This created a dicistronic mRNA sequence, which coded for a truncated amino portion of the sbss polypeptide and a complete NPTII polypeptide. Expression of the NPTII polypeptide was the first proof that a dicistronic mRNA can be translated within plant cells.

The sbss promoter is contained in plasmid pMON154, described below. A culture of E. coli containing this plasmid has been deposited with the American Type Culture Center. This culture has been assigned accession number 39265.

Creation of BGH Chimeric Genes

In an alternate preferred embodiment of this invention, a chimeric gene was created comprising (1) a sbss promoter region and 5' non-translated region, (2) a structural sequence which codes for bovine growth hormone (BGH) and (3) a NOS 3' non-translated region. This chimeric gene was created as follows.

Figure 19:
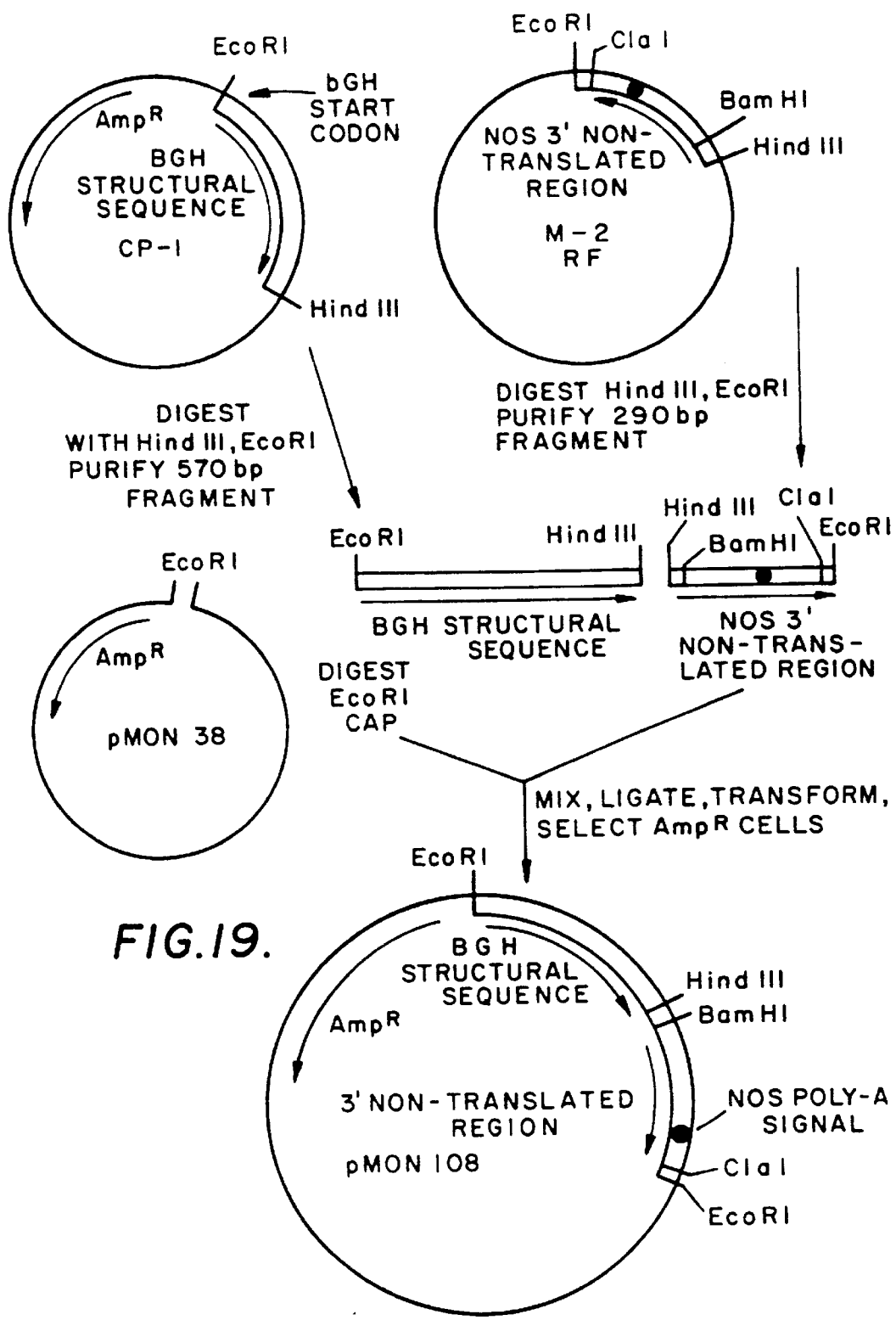
FIG. 19 represents the creation of plasmid pMON108, containing a bovine growth hormone structural sequence and a NOS 3' region.

A structural sequence which codes for the polypeptide, bovine growth hormone, (see, e.g., Woychik et al., 1982) was inserted into a pBR322-derived plasmid. The resulting plasmid was designated as plasmid CP-1. This plasmid was digested with EcoRI and HindIII to yield a 570 bp fragment containing the structural sequence. Double stranded M-2 RF DNA (described previously and shown in FIG. 8) was cleaved with EcoRI and HindIII to yield a 290 bp fragment which contained the NOS 3' non-translated region with a poly-adenylation signal. The two fragments were ligated together and digested with EcoRI to create an 860 base pair fragment with EcoRI ends, which contained a BGH-coding structural sequence joined to the NOS 3' non-translated region. This fragment was introduced into plasmid pMON38, which had been digested with EcoRI and treated with alkaline phosphatase, to create a new plasmid, designated as pMON108, as shown in FIG. 19.

Figure 20:
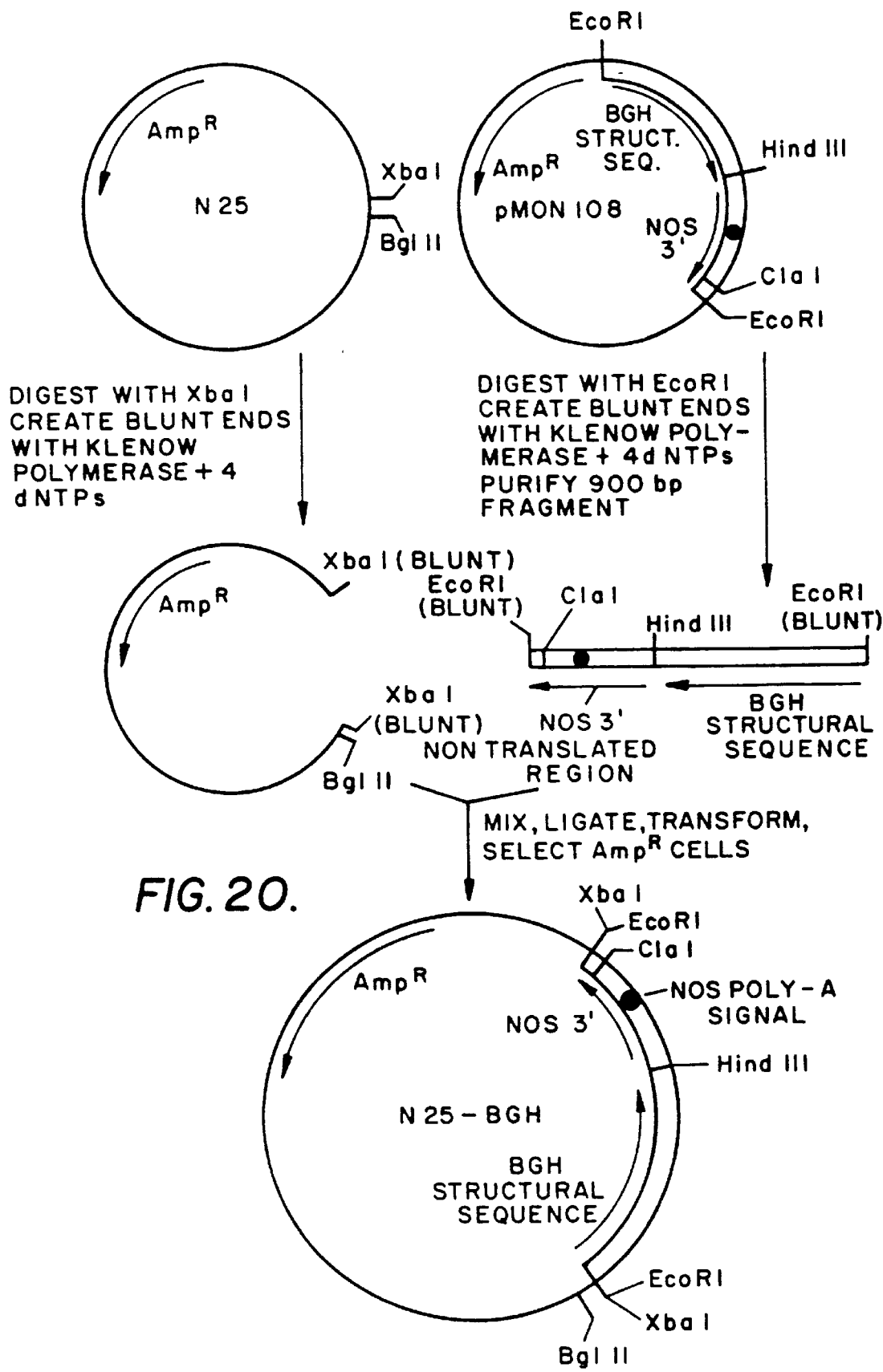
FIG. 20 represents the creation of plasmid N25-BGH, which contains the BGH-NOS sequence surrounded by selected cleavage sites.

A unique BglII restriction site was introduced at the 5' end of the BGH structural sequence by digesting PMON 108 with EcoRI to obtain the 860 bp fragment, and using Klenow polymerase to create blunt ends on the resulting EcoRI fragment. This fragment was ligated into plasmid N25 (a derivative of pBR327 containing a synthetic linker carrying BglII and XbaI cleavage sites inserted at the BamHI site), which had been cleaved with XbaI and treated with Klenow polymerase to obtain blunt ends (N25 contains a unique BglII site located 12 bases from the XbaI site). The resulting plasmid, which contained the 860 bp BGH-NOS fragment in the orientation shown in FIG. 20, was designated as plasmid N25-BGH. This plasmid contains a unique BglII cleavage site located about 25 bases from the 5' end of the BGH structural sequence.

Figure 21:
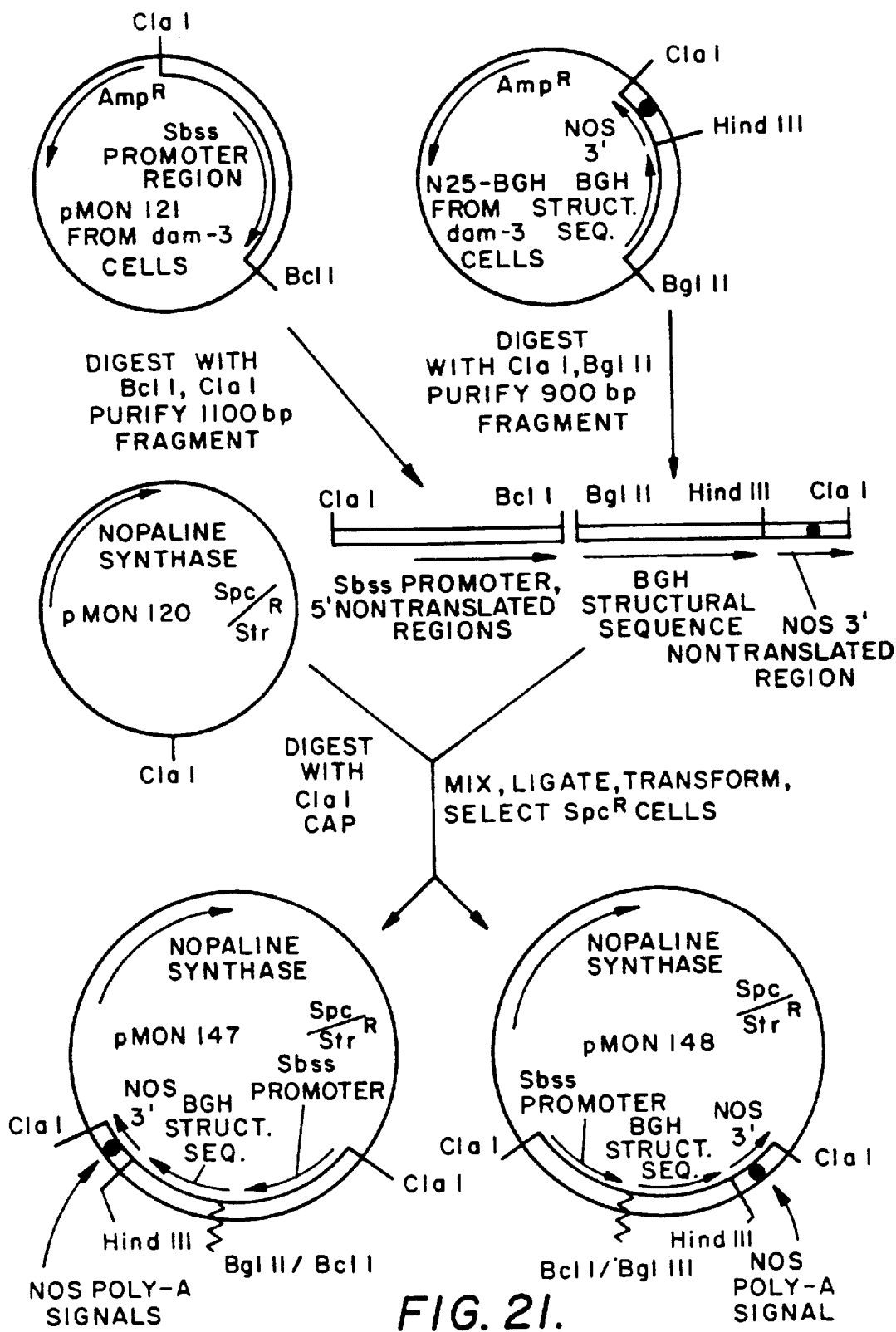
FIG. 21 represents the insertion of a chimeric sbss-BGH-NOS gene into pMON120 to obtain plasmids pMON147 and pMON148.

Plasmid N25-BGH prepared from dam$^-$ E. coli cells was digested with BglII and ClaI to yield an 860 bp fragment which contained the BGH structural sequence joined to the NOS 3' non-translated region. Separately, plasmid pMON121 (described previously and shown in FIG. 17) was prepared from dam$^-$ E. coli cells and was digested with ClaI and BclI to create an 1100 bp fragment which contained the sbss promoter region. The fragments were ligated at their compatible BclI/BglII overhangs, and digested with ClaI to yield a ClaI fragment of about 2 kb containing the chimeric sbss-BGH-NOS gene. This fragment was inserted into pMON120 (described previously and shown in FIG. 10) which had been digested with ClaI. The resulting plasmids, containing the inserted chimeric gene in opposite orientations were designated pMON147 and pMON148, as shown in FIG. 21.

Figure 22:
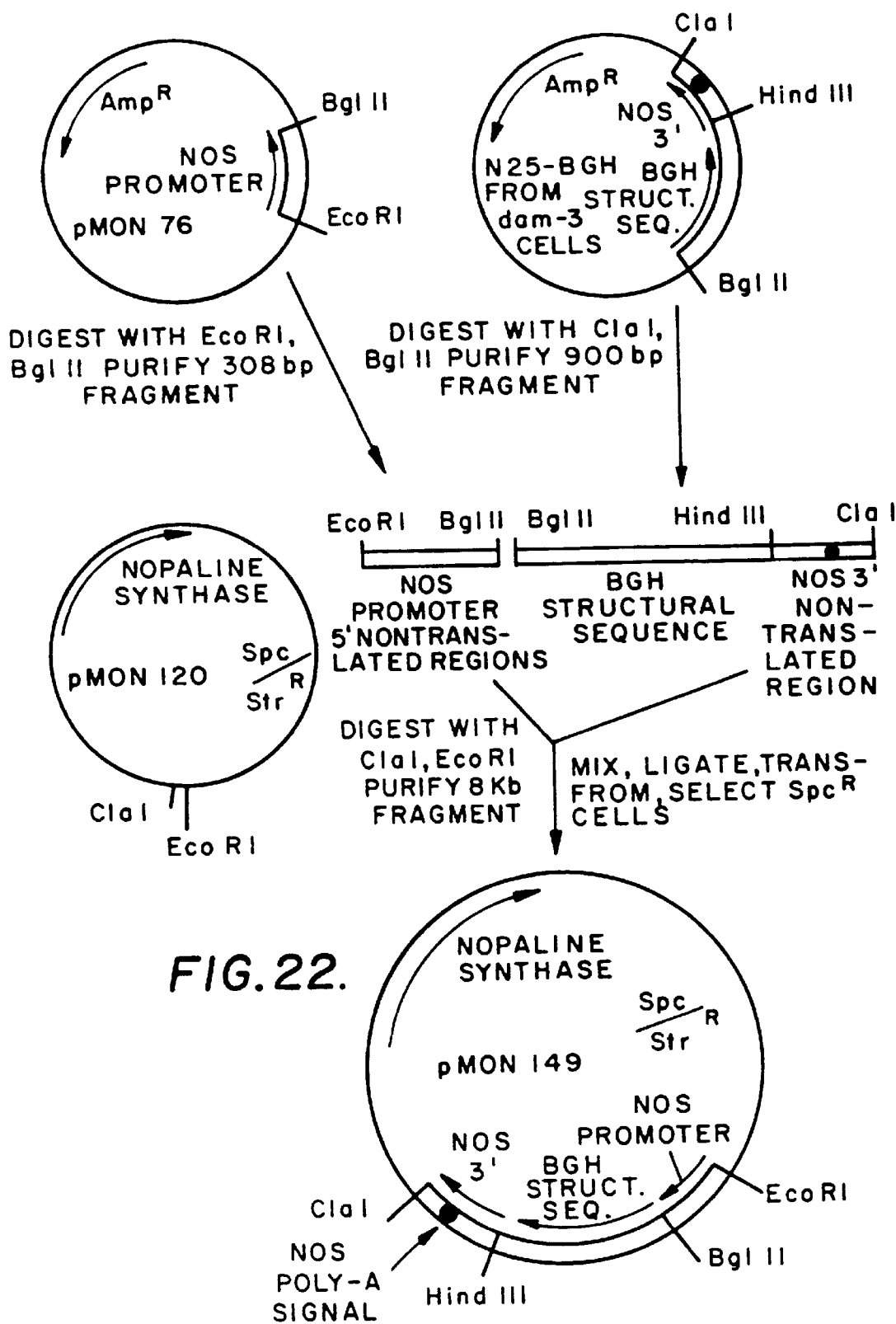
FIG. 22 represents the creation of plasmid pMON149, which contains a chimeric NOS-BGH-NOS gene.

An alternate chimeric BGH gene was created which contained (1) a NOS promoter region and 5' non-translated region, (2) a structural sequence which codes for BGH, and (3) a NOS 3' non-translated region, by the following method, shown in FIG. 22.

Plasmid pMON76 (described above and shown in FIG. 9) was digested with EcoRI and BglII to obtain a 308 bp fragment containing a NOS promoter region and 5' non-translated region. Plasmid N25-BGH prepared from dam$^-$ E. coli cells (described above and shown in FIG. 20) was digested with BglII and ClaI to obtain a 900 bp fragment containing a BGH structural sequence and a NOS 3' non-translated region. These two fragments were ligated together to obtain a chimeric NOS-BGH-NOS gene in a fragment with EcoRI and ClaI ends. This fragment was ligated with an 8 kb fragment obtained by digesting pMON120 with EcoRI and Cla. The resulting plasmid, designated as pMON149, is shown in FIG. 22.

Creation of Chimeric NOS-EPSP-NOS Gene

In an alternate preferred embodiment, a chimeric gene was created comprising (1) a NOS promoter region and 5' non-translated region, (2) a structural sequence which codes for the E. coli enzyme, 5-enolpyruvylshikimate-3-phosphoric acid synthase (EPSP synthase) and (3) a NOS 3' non-translated region.

EPSP synthase is believed to be the target enzyme for the herbicide, glyphosate, which is marketed by Monsanto Company under the registered trademark, "Roundup." Glyphosate is known to inhibit EPSP synthase activity (Amrhein et al., 1980), and amplification of the EPSP synthase gene in bacteria is known to increase their resistance to glyphosate. Therefore, increasing the level of EPSP synthase activity in plants may confer resistance to glyphosate in transformed plants. Since glyphosate is toxic to most plants, this provides for a usefull method of weed control. Seeds of a desired crop plant which has been transformed to increase EPSP synthase activity may be planted in a field. Glyphosate may be applied to the field at concentrations which will kill all non-transformed plants, leaving the non-transformed plants unharmed.

An EPSP synthase gene may be isolated by a variety of means, including the following. A lambda phage library may be created which carries a variety of DNA fragments produced by HindIII cleavage of E. coli DNA. See, e.g., Maniatis et al., 1982.

The EPSP synthase gene is one of the genes which are involved in the production of aromatic amino acids. These genes are designated as the "aro" genes; EPSP synthase is designated as aroA. Cells which do not contain functional aro genes are designated as aro$^-$ cells. Aro$^-$ cells must normally be grown on media supplemented by aromatic amino acids. See Pittard and Wallis, 1966.

Different lambda phages which carry various HindIII fragments may be used to infect mutant E. coli cells which do not have EPSP synthase genes. The infected aro$^-$ cells may be cultured on media which does not contain the aromatic amino acids, and transformed aro$^+$ clones which are capable of growing on such media may be selected. Such clones are likely to contain the EPSP synthase gene. Phage particles may be isolated from such clones, and DNA may be isolated from these phages. The phage DNA may be cleaved with one or more restriction endonucleases, and by a gradual process of analysis, a fragment which contains the EPSP synthase gene may be isolated.

Figure 23:
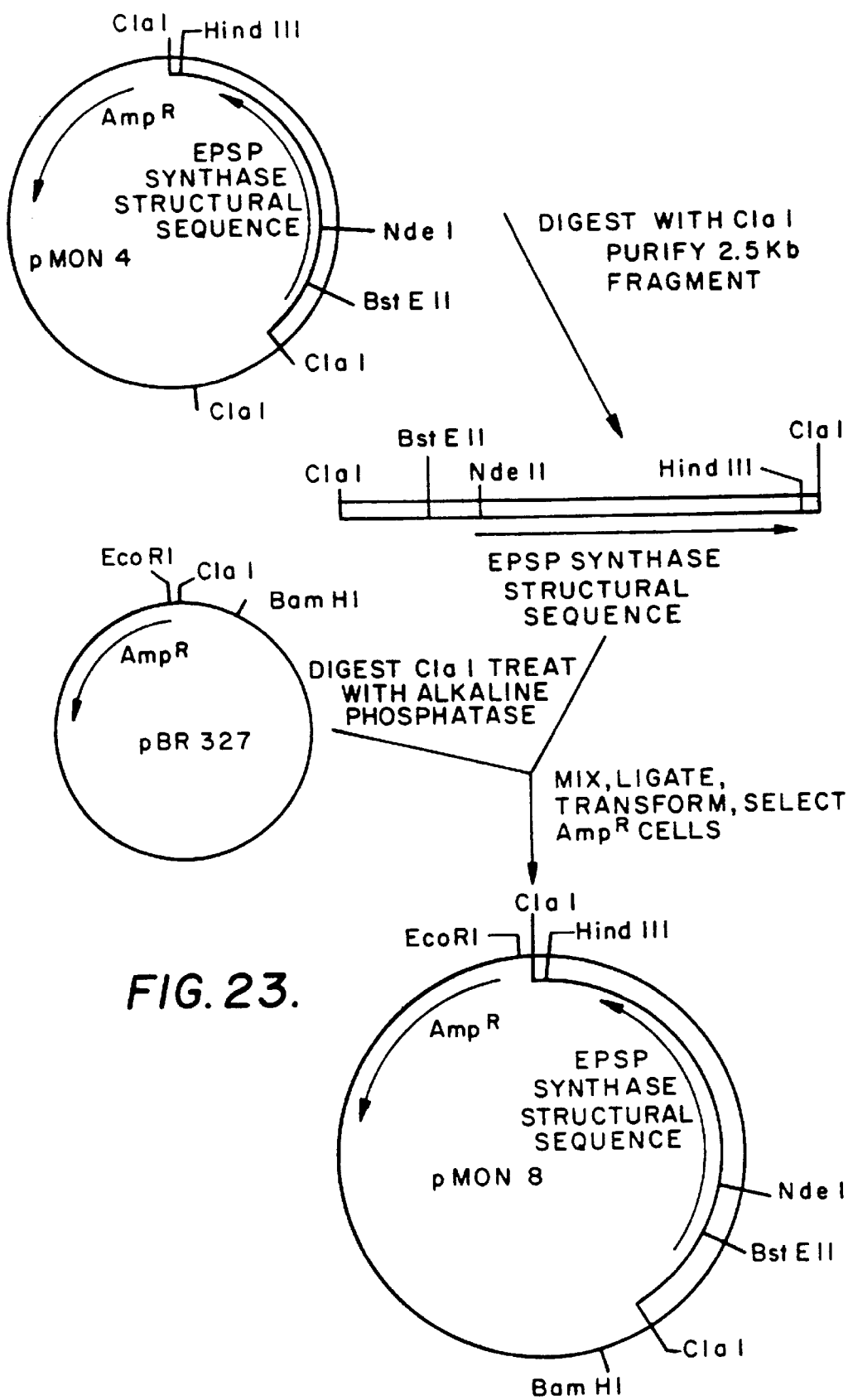
FIG. 23 represents the creation of plasmid pMON8, which contains a structural sequence for EPSP synthase.

Using a procedure similar to the method summarized above, the Applicants isolated an 11 kb HindIII fragment which contained the entire E. coli EPSP synthase gene. This fragment was digested with BglII to produce a 3.5 kb HindIII-BglII fragment which contained the entire EPSP synthase gene. This 3.5 kb fragment was inserted into plasmid pKC7 (Rao and Rogers, 1979) to produce plasmid pMON4, which is shown in FIG. 23.

Plasmid pMON4 was digested with ClaI to yield a 2.5 kb fragment which contained the EPSP synthase structural sequence. This fragment was inserted into pBR327 that had been digested with ClaI, to create pMON8, as shown in FIG. 23.

pMON8 was digested with BamHI and NdeI to obtain a 4.9 kb fragment. This fragment lacked about 200 nucleotides encoding the amino terminus of the EPSP synthase structural sequence.

Figure 24:
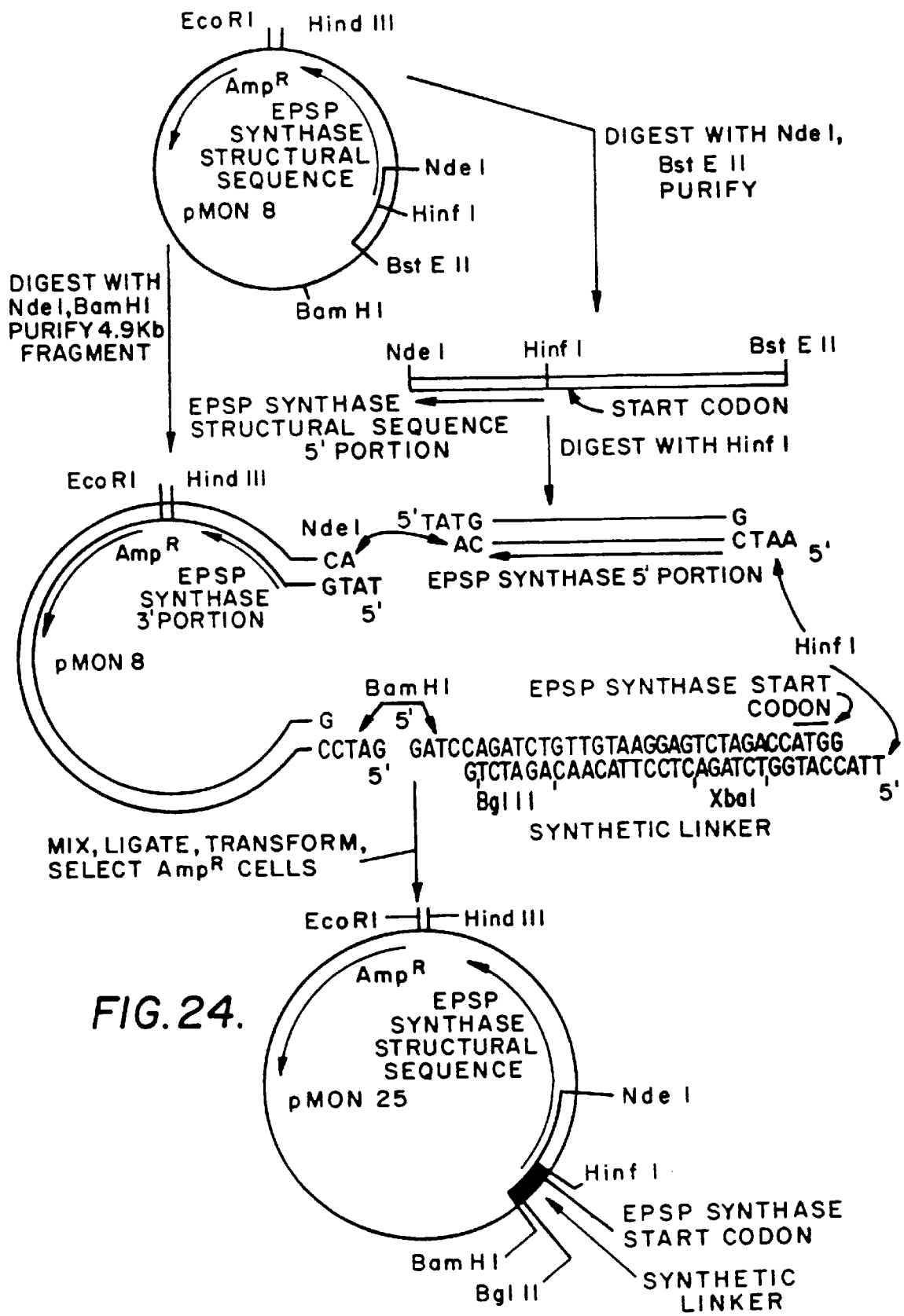
FIG. 24 represents the creation of plasmid pMON25, which contains an EPSP synthase structural sequence with several cleavage sites near the start codon.

The missing nucleotides were replaced by ligating a HinfI/NdeI fragment, obtained from pMON8 as shown in FIG. 24, together with a synthetic oligonucleotide sequence containing (1) the EPSP synthase start codon and the first three nucleotides, (2) a unique BglII site, and (3) the appropriate BamHI and HinfI ends. The resulting plasmid, pMON25, contains an intact EPSP synthase structural sequence with unique BamHI and BglII sites positioned near the start codon.

Figure 25:
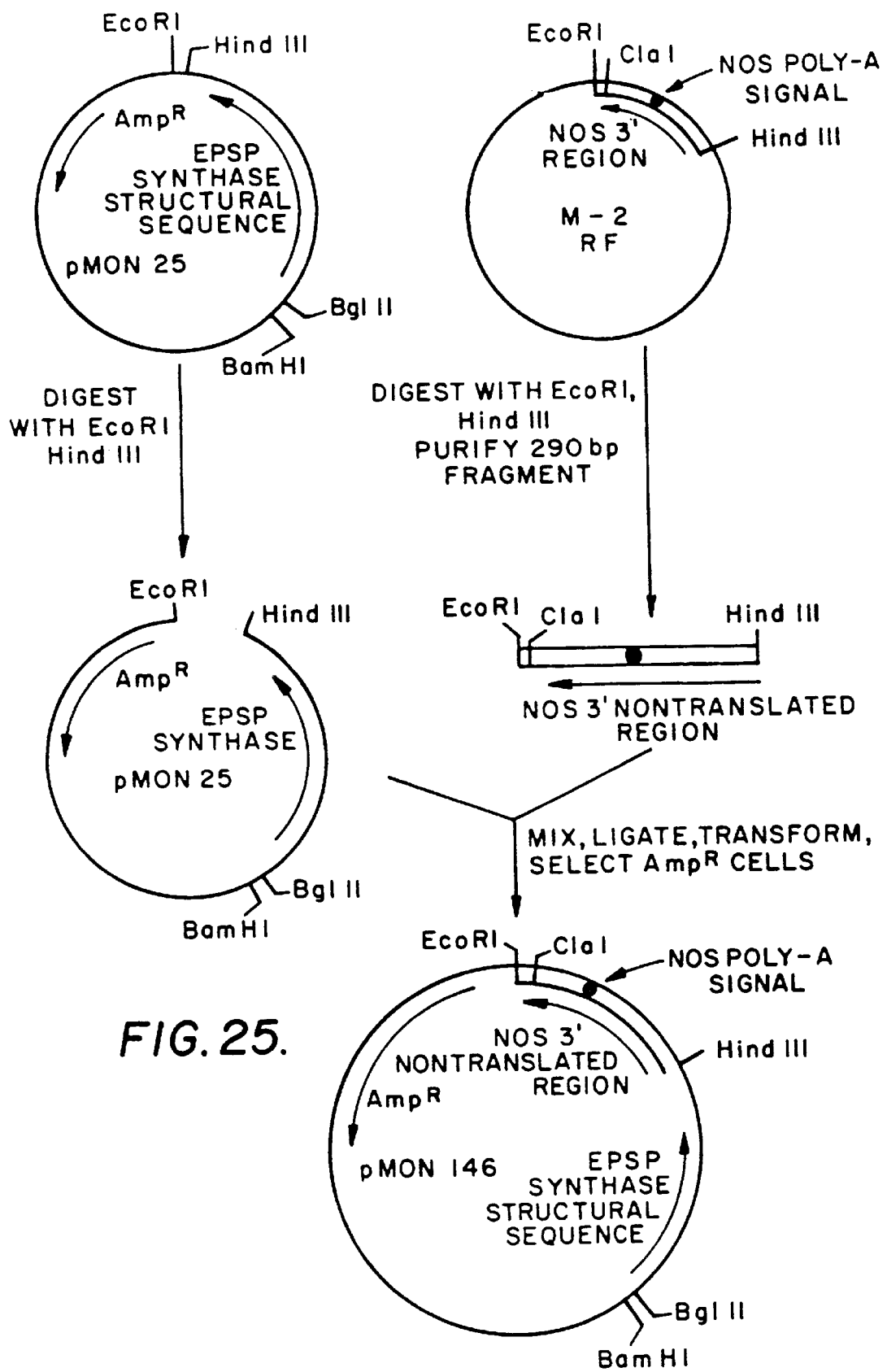
FIG. 25 represents the creation of plasmid pMON146, which contains a chimeric sequence comprising EPSP synthase and a NOS 3' region.
Figure 26:
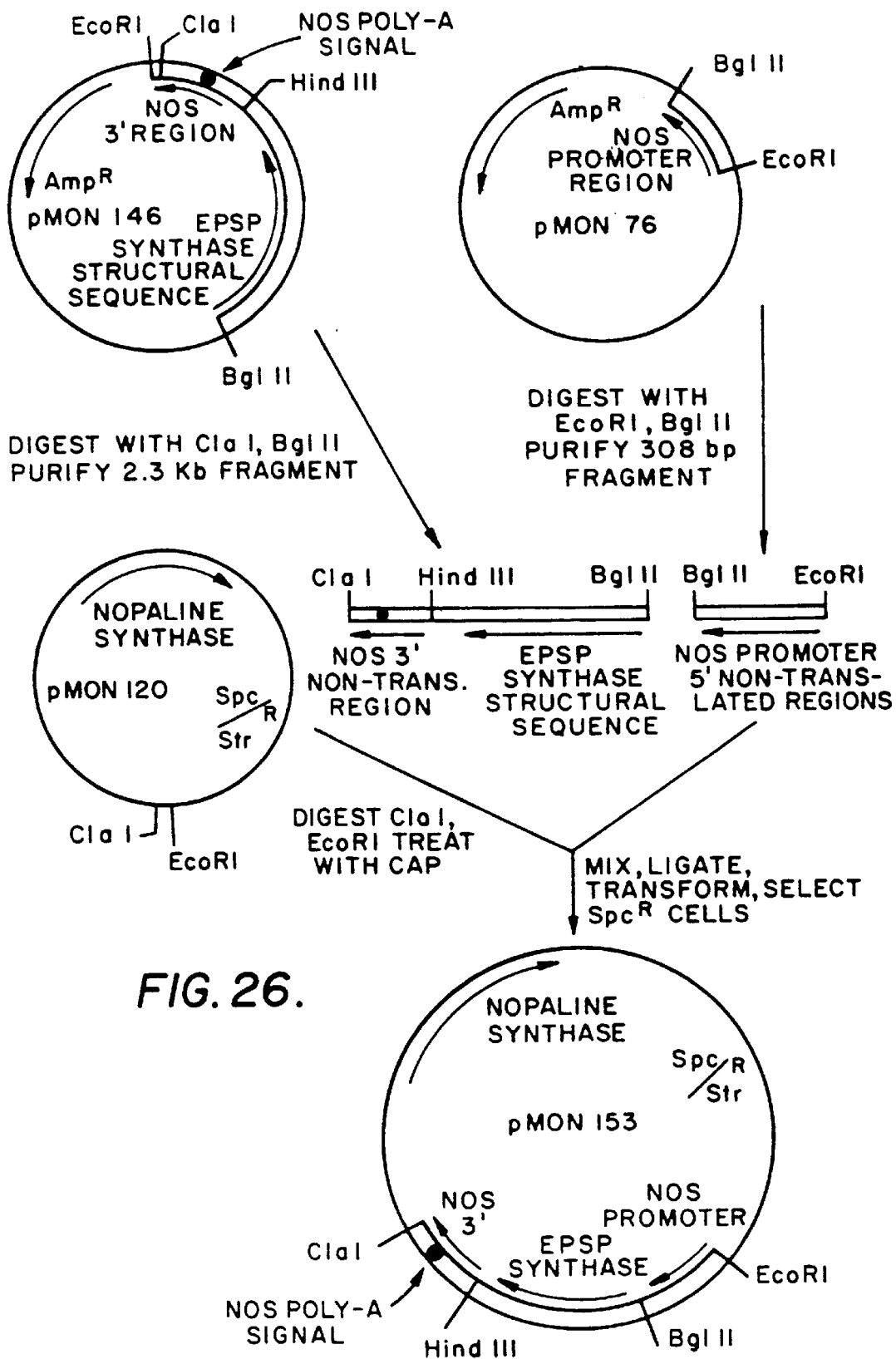
FIG. 26 represents the insertion of a chimeric NOS-EPSP-NOS gene into pMON120 to obtain plasmid pMON153.

Double stranded M-2 DNA (described previously and shown in FIG. 8) was digested with HindIII and EcoRI to yield a 290 bp fragment which contains the NOS 3' non-translated region and poly-adenylation signal. This fragment was introduced into a pMON25 plasmid that had been digested with EcoRI and HindIII to create a plasmid, designated as pMON146 (shown in FIG. 25) which contains the EPSP structural sequence joined to the NOS 3' non-translated region.

pMON146 was cleaved with ClaI and BglII to yield a 2.3 kb fragment carrying the EPSP structural sequence joined to the NOS 3' non-translated region. pMON76 (described previously and shown in FIG. 9) was digested with BglII and EcoRI to create a 310 bp fragment containing the NOS promoter region and 5' non-translated region. The above fragments were mixed with pMON120 (described previously and shown in FIG. 10) that had been digested with ClaI and EcoRI, and the mixture was ligated. The resulting plasmid, designated pMON153, is shown in FIG. 26. This plasmid contains the chimeric NOS-EPSP-NOS gene.

A plasmid containing a chimeric sbss-EPSP-NOS gene was prepared in the following manner, shown in FIG. 27. Plasmid pMON146 (described previously and shown in FIG. 25) was digested with ClaI and BglII, and a 2.3 kb fragment was purified. This fragment contained the EPSP synthase structural sequence coupled to a NOS 3' non-translated region with a poly-adenylation signal. Plasmid pMON121 (described above and shown in FIG. 17) was digested with ClaI and BclI, and a 1.1 kb fragment was purified. This fragment contains an sbss promoter region and 5' non-translated region. The two fragments were mixed and ligated with T4 DNA ligase and subsequently digested with ClaI. This created a chimeric sbss-EPSP-NOS gene, joined through compatible BglII and BclI termini. This chimeric gene with ClaI termini was inserted into plasmid pMON120 which had been digested with ClaI and treated with calf alkaline phosphatase (CAP). The mixture was ligated with T4 DNA ligase. The resulting mixture of fragments and plasmids was used to transform E. coli cells, which were selected for resistance to spectinomycin. A colony of resistant cells was isolated, and the plasmid in this colony was designated as pMON154, as shown in FIG. 27.

A culture of E. coli containing pMON154 has been deposited with the American Type Culture Center. This culture has been assigned accession number 39265.

Means for Inserting Chimeric Genes into Plant Cells

A variety of methods are known for inserting foreign DNA into plant cells. One such method, utilized by the Applicants, involved inserting a chimeric gene into Ti plasmids carried by A. tumefaciens, and co-cultivating the A. tumefaciens cells with plants. A segment of T-DNA carrying the chimeric gene was transferred into the plant genome, causing transformation. This method is described in detail in two separate, simultaneously-filed in two separate, simultaneously filed applications entitled "Plasmids for Transforming Plant Cells," Monsanto Case Number C-07–21-(133) U.S. Ser. No. 458,411, filed Jan. 17, 1983 now abandoned, and "Genetically Transformed Plants," Monsanto Case Number C-07–21-(134) U.S. Ser. No. 458,402, filed Jan. 17, 1983 now abandoned. The contents of both of those applications are hereby incorporated by reference.

A variety of other methods are listed below. These methods are theoretically capable of inserting the chimeric genes of this invention into plant cells, although the reported transformation efficiencies achieved to date by such methods have been low. The chimeric genes of this invention (especially those chimeric genes such as NPTI and NPTII, which may be utilized as selectable markers) are likely to facilitate research on methods of inserting DNA into plants or plant cells.

1. One alternate technique for inserting DNA into plant cells involves the use of lipid vesicles, also called liposomes. Liposomes may be utilized to encapsulate one or more DNA molecules. The liposomes and their DNA contents may be taken up by plant cells; see, e.g., Lurquin, 1981. If the inserted DNA can be incorporated into the plant genome, replicated, and inherited, the plant cells will be transformed.

To date, efforts to use liposomes to deliver DNA into plant cells have not met with great success (Fraley and Papahadjopoulos, 1981). Only relatively small DNA molecules have been transferred into plant cells by means of liposomes, and none have yet been expressed. However, liposome-delivery technology is still being actively developed, and it is likely that methods will be developed for transferring plasmids containing the chimeric genes of this invention into plant cells by means involving liposomes.

2. Other alternate techniques involve contacting plant cells with DNA which is complexed with either (a) polycationic substances, such as poly-L-ornithine (Davey et al., 1980), or (b) calcium phosphate (Krens et al., 1982). Although efficiencies of transformation achieved to date have been low, these methods are still being actively researched.

3. A method has been developed involving the fusion of bacteria, which contain desired plasmids, with plant cells. Such methods involve converting the bacteria into spheroplasts and converting the plant cells into protoplasts. Both of these methods remove the cell wall barrier from the bacterial and plant cells, using enzymic digestion. The two cell types can then be fused together by exposure to chemical agents, such as polyethylene glycol. See Hasezawa et al., 1981. Although the transformation efficiencies achieved to date by this method have been low, similar experiments using fusions of bacterial and animal cells have produced good results; see Rassoulzadegan et al., 1982.

4. Two other methods which have been used successfully to genetically transform animal cells involve (a) direct microinjection of DNA into animal cells, using very small glass needles (Capecchi, 1980), and (b) electric-current-induced uptake of DNA by animal cells (Wong and Neumann, 1982). Although neither of these techniques have been utilized to date to transform plant cells, they may be useful to insert numeric genes of this invention into plant cells.

Use of Chimeric Genes to Identify Plant Regulators

The chimeric genes of this invention may be used to identify, isolate, and study DNA sequences to determine whether they are capable of promoting or otherwise regulating the expression of genes within plant cells.

For example, the DNA from any type of cell can be fragmented, using partial endonuclease digestion or other methods. The DNA fragments are mixed with multiple copies of a chimeric gene which has been cleaved at a unique cleavage site that is located in the 5' direction from the ATG start codon of the structural sequence. Preferably, the structural sequence, if properly transcribed, will be translated into a selectable marker, such as a polypeptide which confers resistance on the host to a selected antibiotic. The DNA mixture is ligated to form plasmids, and the plasmids are used to transform plant cells which are sensitive to the selected antibiotic. The cells are cultured on media which contains an appropriate concentration of the selected antibiotic. Plant cells will survive and reproduce only if the structural sequence is transcribed and translated into the polypeptide which confers resistance to the antibiotic. This is presumed to occur only if the inserted DNA fragment performs the function of a gene promoter; the resistant colonies will be evaluated further to determine whether this is the case.

Using this technique, it is possible to evaluate the promoter regions of bacteria, yeast, fungus, algae, other microorganisms, and animal cells, to determine whether they also function as gene promoters in various types of plant cells. It is also possible to evaluate promoters from one type of plant in other types of plant cells. By using similar methods and varying the cleavage site in the chimeric gene, it is possible to evaluate the performance of any DNA sequence as a 5' non-translated region, a 3' non-translated region, or any type of other regulatory sequence.

If desired, a partial chimeric gene may be utilized in this method of evaluating the regulatory effects of various DNA sequences. For example, the NOS promoter region and/or the NOS 5' non-translated region may be deleted from the NOS-NPTII-NOS chimeric gene. This would create a chimeric gene having a unique cleavage site but no promoter region in front of an NPTII structural sequence.

In case the inserted DNA fragment contains a start codon which might (1) alter the reading frame of the structural sequence, or (2) alter the amino terminus of the polypeptide, it is possible to place an oligonucleotide between the cleavage site and the start codon of the structural sequence. The oligonucleotide would contain stop codons in all three reading frames. Therefore, if a start codon was included in the inserted DNA fragment, the gene would be a dicistronic gene. The first polypeptide would be terminated by whichever stop codon happened to be in the reading frame of the inserted start codon. The second start codon would begin the translation of a separate polypeptide, which would be the selectable marker enzyme.

Meaning of Various Phrases

A variety of phrases which are used in the claims must be defined and described to clarify the meaning and coverage of the claims.

The meaning of any particular term shall be interpreted with reference to the text and figures of this application. In particular, it is recognized that a variety of terms have developed which are used inconsistently in the literature. For example, a variety of meanings have evolved for the term "promoter," some of which include the 5' non-translated region and some of which do not. In an effort to avoid problems of interpretation, the Applicants have attempted to define various terms. However, such definitions are not presumed or intended to be comprehensive and they shall be interpreted in light of the relevant literature.

The term "chimeric gene" refers to a gene that contains at least two portions that were derived from different and distinct genes. As used herein, this term is limited to genes which have been assembled, synthesized, or-otherwise produced as a result of man-made efforts, and any genes which are replicated or otherwise derived therefrom. "Man-made efforts" include enzymatic, cellular, and other biological processes, if such processes occur under conditions which are caused, enhanced, or controlled by human effort or intervention; this excludes genes which are created solely by natural processes.

As used herein, a "gene" is limited to a segment of DNA which is normally regarded as a gene by those skilled in the art. For example, a plasmid might contain a plant-derived promoter region and a heterologous structural sequence, but unless those two segments are positioned with respect to each other in the plasmid such that the promoter region causes the transcription of the structural sequence, then those two segments would not be regarded as included in the same gene.

This invention relates to chimeric genes which have structural sequences that are "heterologous" with respect to their promoter regions. This includes at least two types of chimeric genes:

1. DNA of a gene which is foreign to a plant cell. For example, if a structural sequence which codes for mammalian protein or bacterial protein is coupled to a plant promoter region, such a gene would be regarded as heterologous.

2. A plant cell gene which is naturally promoted by a different plant promoter region. For example, if a structural sequence which codes for a plant protein is normally controlled by a low-quantity promoter, the structural sequence may be coupled with a prolific promoter. This might cause a higher quantity of transcription of the structural sequence, thereby leading to plants with higher protein content. Such a structural sequence would be regarded as heterologous with regard to the prolific promoter.

However, it is not essential for this invention that the entire structural sequence be heterologous with respect to the entire promoter region. For example, a chimeric gene of this invention may be created which would be translated into a "fusion protein," i.e., a protein comprising polypeptide portions derived from two separate structural sequences. This may be accomplished by inserting all or part of a heterologous structural sequence into the structural sequence of a plant gene, somewhere after the start codon of the plant structural sequence.

As used herein, the phrase, "a promoter region derived from a specified gene" shall include a promoter region if one or more parts of the promoter region were derived from the specified gene. For example, it might be discovered that one or more portions of a particular plant-derived promoter region (such as intervening region 8, shown on FIG. 1) might be replaced by one or more sequences derived from a different gene, such as the gene that contains the heterologous structural sequence, without reducing the expression of the resulting chimeric gene in a particular type of host cell. Such a chimeric gene would contain a plant-derived association region 2, intervening region 4, and transcription initiation sequence 6, followed by heterologous intervening region 8, 5' non-translated region 10 and structural sequence 14. Such a chimeric gene is within the scope of this invention.

As used herein, the phrase "derived from" shall be construed broadly. For example, a structural sequence may be "derived from" a particular gene by a variety of processes, including the following:

1. The gene may be reproduced by various means such as inserting it into a plasmid and replicating the plasmid by cell culturing, in vitro replication, or other methods, and the desired sequence may be obtained from the DNA copies by various means such as endonuclease digestion;

2. mRNA which was coded for by the gene may be obtained and processed in various ways, such as preparing complementary DNA from the mRNA and then digesting the cDNA with endonucleases;

3. The sequence of bases in the structural sequence may be determined by various methods, such as endonuclease mapping or the Maxam-Gilbert method. A strand of DNA which duplicates or approximates the desired sequence may be created by various methods, such as chemical synthesis or ligation of oligonucleotide fragments.

4. A structural sequence of bases may be deduced by applying the genetic code to the sequence of amino acid residues in a polypeptide.

Usually, a variety of DNA structural sequences may be determined for any polypeptide, because of the redundancy of the genetic code. From this variety, a desired sequence of bases may be selected, and a strand of DNA having the selected sequence may be created.

If desired, any DNA sequence may be modified by substituting certain bases for the existing bases. Such modifications may be performed for a variety of reasons. For example, one or more bases in a sequence may be replaced by other bases in order to create or delete a cleavage site for a particular endonuclease. As another example, one or more bases in a sequence may be replaced in order to reduce the occurrence of "stem and loop" structures in messenger RNA. Such modified sequences are within the scope of this invention.

A structural sequence may contain introns and exons; such a structural sequence may be derived from DNA, or from an mRNA primary transcript. Alternately, a structural sequence may be derived from processed mRNA, from which one or more introns have been deleted.

The Applicants have deposited two cultures of *E. coli* cells containing plasmids pMON128 and pMON154 with the American Type Culture Collection (ATCC). These cells have been assigned ATCC accession numbers 39264 and 39265, respectively. The Applicants have claimed cultures of microorganisms having the "relevant characteristics" of either culture. As used herein, the "relevant characteristics" of a cell culture are limited to those characteristics which make the culture suitable for a use which is disclosed, suggested or made possible by the information contained herein. Numerous characteristics of the culture may be modified by techniques known to those skilled in the art; for example, the cells may be made resistant to a particular antibiotic by insertion of a particular plasmid or gene into the cells, or the pMON128 or pMON154 plasmids might be removed from the designated cells and inserted into a different strain of cells. Such variations are within the scope of this invention, even though they may amount to improvements, which undoubtedly will occur after more researchers gain access to these cell cultures.

Those skilled in the art will recognize, or be able to ascertain using no more than routine experimentation, numerous equivalents to the specific embodiments described herein. Such equivalents are within the scope of this invention.

EXAMPLES

Example 1

Creation of pMON1001

Fifty micrograms (ug) of lambda phage bbkan-1 DNA (Berg et al., 1975) were digested with 100 units of HindIII (all restriction endonucleases were obtained from New England Biolabs, Beverly, Mass., and were used with buffers according to the suppliers instructions, unless otherwise specified) for 2 hours at 37° C. After heat-inactivation (70° C., 10 minutes), the 3.3 kb Tn5 HindIII fragment was purified on gradient. One ug of the purified HindIII fragment was digested with BamHI (2 units, 1 hour, 37° C.), to create a 1.8 kb fragment. The endonuclease was heat inactivated.

Plasmid pBR327 (Soberon et al., 1981), 1 ug, was digested with HindIII and BamHI (2 units each, 2 hours, 37° C.). Following digestion, the endonucleases were heat inactivated and the cleaved pBR327 DNA was added to the BamHI-HindIII Tn5 fragments. After addition of ATP to a concentration of 0.75 mM, 10 units of T4 DNA ligase (prepared by the method of Murray et al., 1979) was added, and the reaction was allowed to continue for 16 hours at 12–14° C. One unit of T4 DNA ligase will give 90% circularization of one ug of HindIII-cleaved pBR327 plasmid in 5 minutes at 22° C.

The ligated DNA was used to transform $CaCl_2$-shocked *E. coli* C600 recA56 cells (Maniatis et al., 1982). After expression in Luria broth (LB) for 1 hour at 37° the cells were spread on solid LB media plates containing 200 ug/ml ampicillin and 40 ug/ml kanamycin. Following 16 hours incubation at 37° C., several hundred colonies appeared. Plasmid mini-prep DNA was prepared from six of these.

(Ish-Horowicz and Burke, 1981). Endonuclease digestion showed that all six of the plasmids carried the 1.8 kb HindIII-BamHI fragment. One of those isolates was designated as pMON1001 as shown in FIG. 6.

Example 2

Creation of pMON40

Five ug of plasmid pMON1001 (described in Example 1) was digested with SmaI. The reaction was terminated by phenol extraction, and the DNA was precipitated by ethanol. A BamHI linker CCGGATCCGG (0.1 ug), which had been phosphorylated with ATP and T4 polynucleotide kinase (Bethesda Research Laboratory, Rockville, Md.) was added to 1 ug of the pMON1001 fragment. The mixture was treated with T4 DNA ligase (100 units) for 18 hours at 14° C. After heating at 70° C. for 10 minutes to inactivate the DNA ligase, the DNA mixture was digested with BamHI endonuclease (20 units, 3 hours, 37° C.) and separated by electrophoresis on an 0.5% agarose gel. The band corresponding to the 4.2 kb SmaI-BamHI vector fragment was excised from the gel. The 4.2 kb fragment was purified by absorption on glass beads (Vogelstein and Gillespie, 1979), ethanol precipitated and resuspended in 20 ul of DNA ligase buffer with ATP. T4 DNA ligase (20 units) was added and the mixture was incubated for 1.5 hours at room temperature. The DNA was mixed with rubidium chloride-shocked in *E. coli* C600 cells for DNA transformation. (Maniatis et al., 1982). After expression for 1 hour at 37° C. in LB, the cells were spread on LB plates containing 200 ug/ml of ampicillin and 20 ug/ml kanamycin. The plates were incubated at 37° C. for 16 hours. Twelve ampicillin-resistant, kanamycin-resistant colonies were chosen, 2 ml cultures were grown, and mini-plasmid preparations were performed. Endonuclease mapping of the plasmids revealed that ten of the twelve contained no SmaI site and a single BamHi site, and were of the appropriate size, 4.2 kb. The plasmid from one of the ten colonies was designated as pMON40, as shown in FIG. 6.

Example 3

Creation of NOS Promoter Fragment

An oligonucleotide with the following sequence, 5'-TGCAGATTATTTGG-3', was synthesized (Beaucage and Carruthers, 1981, as modified by Adams et al., 1982). This oligonucleotide contained a $^{32}P$ radioactive label, which was added to the 5' thymidine residue by polynucleotide kinase.

An M13 mp7 derivative, designated as S1A, was given to Applicants by M. Bevan and M. D. Chilton, Washington University, St. Louis, Mo. To the best of Applicants' knowledge and belief, the S1A DNA was obtained by the following method. A pTiT37 plasmid was digested with HindIII, and a 3.4 kb fragment was isolated and designated as the HindIII-23 fragment. This fragment was digested with Sau3a, to create a 344 bp fragment with Sau3a ends. This fragment was inserted into double-stranded, replicative form DNA from the M13 mp7 phage vector (Messing et al., 1981) which had been cut with BamHI. Two recombinant phages with 344 bp inserts resulted, one of which contained the anti-sense strand of the NOS promoter fragment. That recombinant phage was designated as S1A, and a clonal copy was given to the Applicants.

The Applicants prepared the single-stranded form of the S1A DNA (14. 4 ug, 6 pmol), and annealed it (10 minutes at 70° C., then cooled to room temperature) with 20 pmol of the 14-mer oligonucleotide, mentioned above. The oligonucleotide annealed to the Sau3a insert at bases 286–300 as shown on FIGS. 4 and 5.

200 ul of the S1A template and annealed oligonucleotide were mixed with the four dNTP's (present at a final concentration of lmM, 25 ul) and 50 ul of Klenow polymerase. The mixture incubated for 30 minutes at room temperature. During this period, the polymerase added dNTP's to the 3' end of the oligonucleotide. The polymerase was heat-inactivated (70° C., 3 minutes), and HaeIII (160 units) were added. The mixture was incubated (1 hour, 55° C.), the HaeIII was inactivated (70° C., 3 minutes), and the four dNTP's (1 mM, 12 ul) and T4 DNA polymerase (50 units) were added. The mixture was incubated (1 hour, 37° C.) and the polymerase was inactivated (70° C., 3 minutes). This yielded a fragment of about 570 bp. EcoRI (150 units) was added, the mixture was incubated (1 hour, 37° C.) and the EcoRI was inactivated (70° C., 3 minutes).

Aliquots of the mixture were separated on 6% acrylamide with 25% glycerol. Autoradiography revealed a radioactively labelled band about 310 bp in size. This band was excised. The foregoing procedure is indicated by FIG. 5.

Example 4

Creation of pMON58

Five ug of plasmid pMON40 (described in Example 2) were digested with BglII (10 units, 1.5 hours, 37° C.), and the BglII was inactivated (70° C., 10 minutes). The four dNTP's (1 mM, 5 ul) and Klenow polymerase (8 units) were added, the mixture was incubated (37° C., 40 minutes), and the polymerase was inactivated (70° C., 10 minutes). EcoRI (10 units) was added and incubated (1 hour, 37° C.), and calf alkaline phosphatase (CAP) was added and incubated (1 hour, 37° C.). A fragment of about 3.9 kb was purified on agarose gel using NA-45 membrane (Scheicher and Scheull, Keene NH). The fragment (1.0 pM) was mixed with the NOS promoter fragment (0.1 pM), described in Example 3, and with T4 DNA ligase (100 units). The mixture was incubated (4° C., 16 hours). The resulting plasmids were inserted into *E. coli* cells, which were selected on media containing 200 ug/ml ampicillin. Thirty-six clonal Amp$^R$ colonies were selected, and mini-preps of plasmids were made from those colonies. The plasmid from one colony demonstrated a 308 bp EcoRI-BglII fragment, a new SstII cleavage site carried by the 308 bp NOS fragment, and a new PstI site. This plasmid was designated as pMON58, as shown in FIG. 7. pMON58 DNA was prepared as described above.

Example 5

Creation of pMON42

Plasmid pBR325-HindIII-23, a derivative of plasmid pBR325 (Bolivar, 1978) carrying the HindIII-23 fragment of pTIT37 (see FIG. 3) in the HindIII site, was given to Applicants by M. Bevan and M. D. Chilton, Washington University, St. Louis, Mo. DNA of this plasmid was prepared and 30 ug were digested with HindIII (50 units) and BamHI (50 units). The 1.1 kb HindIII-BamHI fragment was purified by adsorption on glass beads (Vogelstein and Gillespie, 1979) after agarose gel electrophoresis. The purified fragment (0.5 ug) was added to 0.5 ug of the 2.9 kb HindIII-BamHI fragment of pBR327. After treatment with DNA ligase (20 units, 4 hours, 22° C.), the resulting plasmids were introduced to *E. coli* C600 cells. Clones resistant to ampicillin at 200 ug/ml were selected on solid media; 220 clones were obtained. Minipreps of plasmid DNA were made from six of these clones and tested with the presence of a 1.1 kb fragment after digestion with HindIII and BamHI. One plasmid which demonstrated the correct insert was designated pMON42. Plasmid pMON42 DNA was prepared as described in previous examples.

Example 6

Creation of M13 Clone M-2

Seventy-five ug of plasmid pMON42 (described in Example 5) prepared from dam$^-$ *E. coli* cells were digested with RsaI and BamHI (50 units of each, 3 hours, 37° C.) and the 720 bp RsaI-BamHI fragment was purified using NA-45 membrane. Eight ug of the purified 720 bp BamHI-RsaI fragment were digested with MboI (10 minutes, 70° C.), the ends were made blunt by filling in with the large Klenow fragment of DNA polymerase I and the four dNTP's. Then 0.1 ug of the resulting DNA mixture was added to 0.05 ug of M13 mp8 previously digested with SmaI (1 unit, 1 hour 37° C.) and calf alkaline phosphatase (0.2 units). After ligation (10 units of T4 DNA ligase, 16 hours, 12° C.) and transfection of *E. coli* JM101 cells, several hundred recombinant phage were obtained. Duplex RF DNA was prepared from twelve recombinant, phage-carrying clones. The RF DNA (0.1 ug) was cleaved with EcoRI, (1 unit, 1 hour, 37° C.), end-labeled with $^{32}$P-dATP and Klenow polymerase, and re-digested with BamHI (1 unit, 1 hour, 37° C.). The EcoRI and BamHI sites span the SmaI site. Therefore, clones containing the 260 bp MboI fragment could be identified as yielding a labelled 270 bp fragment after electrophoresis on 6% poly-acrylamide gels and autoradiography. Four of the twelve clones carried this fragment. The orientation of the insert was determined by digestion of the EcoRI-cleaved, end-labeled RF DNA (0.1 ug) with HinfI (1 unit, 1 hour, 37° C.). HinfI cleaves the 260 bp MboI fragment once 99 bp from the 3' end of the fragment and again 42 bp from the end nearest the NOS coding region. Two clones of each orientation were obtained. One clone, digested as M-2 as shown in FIG. 8, contained the 260 bp fragment with the EcoRI site at the 3' end of the fragment. M-2 RF DNA was prepared using the procedures of Messing, et al 1981.

Example 7

Creation of pMON75 and pMON76

Fifty ug of M-2 RF DNA (described in Example 6) were digested with 50 units of EcoRI and 50 units of BamHI for 2 hours at 37°. The 270 bp fragment 1(ug) was purified using agarose gel and NA-45 membrane. Plasmid pMON58 (described in Example 4) was digested with EcoRI and BamHI (50 ug, 50 units each, 2 hours, 37° C.) and the 1300 bp fragment was purified using NA-45 membrane. The 270 bp EcoRI-BamHI (0.1 ug) and 1300 bp EcoRI-BamHI (0.5 ug) fragments were mixed, treated with T4 DNA ligase (2 units) for 12 hours at 14° C. After heating at 70° C. for 10 minutes to inactivate the ligase, the mixture was treated with EcoRI (10 units) for 1 hour at 37° C., then heated to 70° C. for 10 minutes to inactivate the EcoRI. This completed the assembly of a chimeric NOS-NPTII-NOS gene on a 1.6 kb fragment, as shown on FIG. 9.

Plasmid pMON38 is a clone of the pTiT37 HindIII-23 fragment inserted in the HindIII site of pBR327 (Soberon et al., 1980). pMON38 DNA (20 ug) was digested with EcoRI (20 units, 2 hours, 37° C.) and calf alkaline phosphatase (0.2 units, 1 hour, 37° C.). The pMON38 DNA reaction was extracted with phenol, precipitated with ethanol, dried and resuspended in 20 ul of 10 mM Tris-HCl, 1 mM EDTA, pH 8.

0.2 ug of the cleaved pMON38 DNA was added to the chimeric gene mixture described above. The mixture was treated with T4 DNA ligase (4 units, 1 hour, 22° C.) and mixed with Rb chloride-treated *E. coli* C600 recA56 cells to obtain transformation. After plating with selection for ampicillin-resistant (200 ug/ml) colonies, 63 potential candidates were obtained. Alkaline mini-preps of plasmid DNA were made from 12 of these and screened by restriction endonuclease digestion for the proper constructs. Plasmid DNA's that contained a 1.5 kb EcoRI fragment and a new BglII site were digested with BamHI to determine the orientation of the 1.5 kb EcoRI fragment. One of each insert orientation was picked. One plasmid was designated pMON75 and the other pMON76, as shown in FIG. 9. DNA from these plasmids were prepared as described in previous examples.

Example 8

Creation of plasmids pMON128 and pMON129

Figure 10:
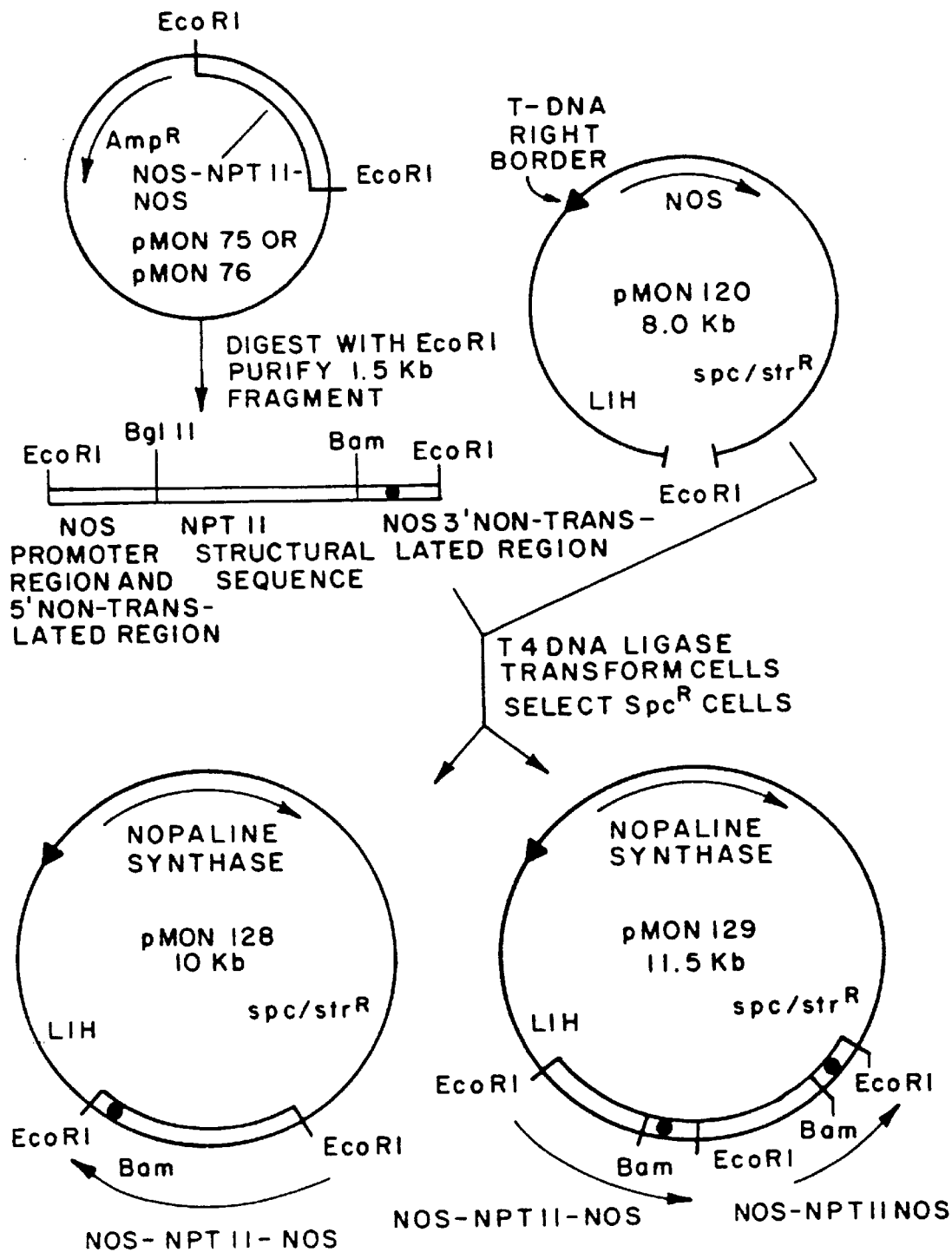
FIG. 10 represents the insertion of the NOS-NPTII-NOS chimeric gene into plasmid pMON120 to obtain plasmids pMON128 and pMON129.

The 1. 5 kb EcoRI fragment was excised by EcoRI digestion from either pMON75 or pMON76 and purified after agarose gel electrophoresis as described in previous examples. Five ug of DNA from plasmid pMON120 was digested with EcoRI and treated with calf alkaline phosphatase. After phenol deproteinization and ethanol precipitation, the EcoRI-cleaved pMON120 linear DNA was mixed with 0.5 ug of the 1.5 kb EcoRI chimeric gene fragment. The mixture was treated with 2 units of T4 DNA ligase for 1 hour at 22° C. After transformation of *E. coli* cells and (Maniatis, et al., 1982) selection of colonies resistant to spectinomycin (50 ug/ml), several thousand colonies appeared. Six of these were picked, grown, and plasmid mini-preps made. The plasmid DNA's were digested with EcoRI to check for the 1.5 kb chimeric gene insert and with BamHI to determine the orientation of the insert. BamHI digestion showed that in pMON128 the chimeric gene was transcribed in the same direction as the intact nopaline synthase gene of pMON120. The orientation of the insert in pMON129 was opposite that in pMON128; the appearance of an additional 1.5 kb BamHI fragment in digests of pMON129 showed that plasmid pMON129 carried a tandem duplication of the chimeric NOS-NPTII-NOS gene, as shown in FIG. 10.

REFERENCES

Adams, S. et al., Abstract #149, 183rd Meeting of the Amer. Chemical Society (1982)
Amrhein, N. et al., *Plant Physiol.* 66: 830 (1980)
Auerswald, E. et al., *Cold Spr. Hbr. Symp. Quant Biol.* 45: 107 (1981)
Bale, A. et al., *Mut. Res.* 59: 157 (1979)
S. Beaucage and M. Carruthers, *Tetrahedron Lett.* 22: 1859 (1981)
Beck, E. et al., *Gene* 19: 327 (1982)
Beggs, J., *Nature* 275: 104 (1978)
Berg, D. et al., *Proc. Natl. Acad. Sci. USA* 76: 3628 (1975)
Bolivar, F., *Gene* 4: 121 (1978)
Capecchi, M., *Cell* 22: 479 (1980)
Chang, A. C. Y. and S. U. Cohen, *J. Bacteriol.* 134: 1141–1156 (1978)
Colbere-Garapin, F. et al., *J. Mol. Biol.* 150: 1–14 (1981)
Covey, S. N., G. P. Lomonosoff and R. Hull (1981) *Nucleic Acids Res.* 9, 6735–6747
Currier, T. and E. Nester, *J. Bact.* 126: 157 (1976)
Davey, M. et al., *Plant Sci. Lett.* 18: 307 (1980)
Ditta, G. et al., *Proc. Natl. Acad. Sci. USA* 77: 7347 (1980)
Dudley, R. et al. *Virology* 117:19 (1982)
Fischer, R. and R. Goldberg, *Cell* 29: 651 (1982)
Fraley, R. and D. Papahadjopoulos, *Current Topics in Microbiology and Immunology* 96: 171 (1981)
Fraley, R. T., R. B. Horsch, A. Matzke, M. D. Chilton, W. S. Chilton and P. R. Sanders, *Plant Molecular Biology* 3, 371–378 (1984)
Frank, A., H. Guilley, G. Joward, K. Richards and L. Hirth, *Cell* 21,285–294 (1980)
Gardner, R. C. et al., *Nucleic Acids Research* Vol 9, No. 12: 287 (1981)
Garfinkel, D. et al., *Cell* 27: 143 (1981)
Guarente, L. et al., *Science* 209: 1428–1430 (1980)
Hasezawa, S. et al., *Mol. Gen. Genet.* 182: 206 (1981)
Hernalsteens, J. et al., *Nature* 287: 654 (1980)
Howarth, A. S. et al., *Virology* 112:678 (1981)
Hyldig-Nielsen, J., *Nucleic Acids Res.* 10: 689 (1982)
Ish-Horowicz, D. and J. Burke, *Nucleic Acids Res* 9: 2989 (1981)
Itakura, K et al., *Science* 198: 1056–1063 (1977)
Jimenez, A. and J. Davies, *Nature* 287: 869 (1980)
Kozak, M. *Cell* 15: 1109 (1978)
Krens, F. et al., *Nature* 296: 72 (1982)
Leemans, J. et al., *J. Mol. Appl. Genet.* 1: 149 (1981)
Leemans, J. et al., *The EMBO J.* 1: i47 (1982)
Lehninger, A., *Biochemistry*. 2nd edition (Worth Publishers, New York, 1975)
Lurquin, P., *Nucleic Acids Res.* 6: 3773 (1979)
Maniatis, T. et al., *Molecular Cloning—A Laboratory Manual* (Cold Spring Harbor Laboratory, 1982)
Matzke, T. and M.-D. Chilton, *J. Mol. Appl-. Genet.*: 39 (1981)
McKnight, S., *Cell* 31: 355 (1982)
Messing, J. et al., *Nucleic Acids Res.* 9: 309 (1981)
Miller, J., *Experiments in Molecular Genetics*. Cold Spring Harbor Laboratory, N.Y. (1972)
Miller, J. and W. Reznikof, *The Operon*, 2nd edition, Cold Spring Harbor Laboratory, New York (1982)
Murray, N. et al., *J. Mol. Biol.* 132: 493 (1979)
Pederson, H. et al., *Cell* 29: 1015 (1982)
Petit, A. and J. Tempe, *Mol. Gen. Genet.* 167: 145 (1978)
Pittard, J. and B. Wallace, *J. Bacteriol.* 91: 1494 (1966)
Radding, C. M., *Annu. Rev. Biochem.* 47: 847–880 (1978)
Rao, N. and S. Rogers, *Gene* 7: 79 (1979)
Rassoulzadegan, M. et al., *Nature* 295: 257 (1982)
Roberts, T. et al., *Proc. Natl. Acad. Sci. USA* 76: 760 (1979)
Sakaguchi, S. and M. Okanishi, *Molecular Breeding and Genetics of Applied Microorganisms*, Kodansha/Academic Press (1981)
Sciaky, D. et al., *Plasmid* 1: 238 (1978)
Setlow, J. and A. Hollaender, *Genetic Engineering*. Plenum Press, New York; volumes 1–4
Shah, D. et al., *Proc. Natl. Acad. Sci. USA* 79: 1022 (1982)
Shibata, T. et al., *Proc. Natl. Acad. Sci. USA* 76: 1638–1642 (1979)
Soberon, X. et al., *Gene* 9: 287 (1980)
Southern, P. and P. Berg, *J. Mol. Appl. Gen.* 1: 327–341 (1982)
Struhl, K. et al., *Proc. Natl. Acad. Sci. USA* 75: 1929 (1979)
Stryer, L., *Biochemistry*, 2nd edition (Freeman & Co., San Francisco, 1981)

Vieira, J. and J. Messing, *Gene* 19: 259 (1982)
Vogelstein, C. and G. Gillespie, *Proc. Natl. Acad. Sci.* USA 76: 615 (1979)
Wong, T. K and E. Neumann, *Bioch. Biophys. Res. Comm.* 107: 584 (1982)
Woychik, R. et al., *Nucleic Acids Res.* 10: 7197 (1982)

What is claimed is:

1. A chimeric plant-expressible gene, said gene comprising in the 5' to 3' direction:

(a) a promoter region derived from a gene that is naturally expressed in a plant cell and that is capable of effecting mRNA transcription in the selected plant cell to be transfonned, operably linked to (b) a structural DNA sequence encoding a polypeptide that permits the selection of transformed plant cells containing said chimeric gene by rendering said transformed plant cells resistant to an amount of an antibiotic that would be toxic to non-transformed plant cells, operably linked to (c) a non-translated region of a gene naturally expressed in plant cells, said region encoding a signal sequence for polyadenylation of mRNA.

2. The gene of claim 1 in which the polypeptide renders transformed plant cells resistant to an amount of an aminoglycoside antibiotic that would be toxic to non-transformed plant cells.

3. The gene of claim 2 in which the polypeptide is a neomycin phosphotransferase polypeptide.

4. The gene of claim 1 in which the non-translated region is selected from a gene from the group consisting of the genes of the T-DNA region of *Agrobacterium tumefaciens*.

5. The gene of claim 4 in which the non-translated region is from the nopaline synthase gene of *Agrobacterium tumefaciens*.

6. The gene of claim 3 wherein said polypeptide is a neomycin phosphotransferase I polypeptide.

7. The gene of claim 3 wherein said polypeptide is a neomycin phosphotransferase II polypeptide.

8. A chimeric gene capable of expressing a polypeptide in plant cells comprising in sequence (a) a promoter region from a gene which is naturally expressed in plant cells;

(b) a 5' non-translated region;

(c) a structural coding sequence encoding a neomycin phosphotransferase polypeptide; and (d) a 3' non-translated region of a gene naturally expressed in plant cells, said region encoding a signal sequence for polyadenylation of mRNA.

9. The gene of claim 8 in which the 3' non-translated region is selected from a gene from the group consisting of the genes of the T-DNA region of *Agrobacterium tumefaciens*.

10. The gene of claim 9 in which the non-translated region is from the nopaline synthase gene of *Agrobacterium tumefaciens*.

11. The gene of claim 8 wherein said polypeptide is a neomycin phosphotransferase I polypeptide.

12. The gene of claim 8 wherein said polypeptide is a neomycin phosphotransferase II polypeptide.

13. A microorganism containing a chimeric gene of claim 1.

14. A microorganism containing a chimeric gene of claim 8.

15. A culture of microorganisms of claim 13.

16. A culture of microorganisms of claim 14.

17. The culture of claim 15 in which the microorganism is *E. coli*.

18. The culture of claim 15 in which the microorganism is *Agrobacterium tumefaciens*.

19. A plant cell susceptible to infection with *Agrobacterium tumefaciens* which contains and expresses a chimeric gene of claim 1.

20. A plant cell susceptible to infection with *Agrobacterium tumefaciens* which contains and expresses a chimeric gene of claim 8.

21. Plant tissue comprising plant cells susceptible to infection with *Agrobacierieim tumefaciens* which contain and express a chimeric gene of claim 1.

22. Plant tissue comprising plant cells susceptible to infection with *Agrobacterium tumefaciens* which contain and express a chimeric gene of claim 8.

23. Plant tissue as in either claim 21 or 22 wherein said tissue comprises undifferentiated tissue.

\* \* \* \* \*

UNITED STATES PATENT AND TRADEMARK OFFICE
CERTIFICATE OF CORRECTION

PATENT NO. : 6,174,724 B1
DATED : January 16, 2001
INVENTOR(S) : Stephen G. Rogers and Robert T. Fraley It is certified that error appears in the above-identified patent and that said Letters Patent is hereby corrected as shown below:

<u>Column 29,</u>
Line 13, delete "transfonned" and insert therefor -- transformed --.

Signed and Sealed this

Twenty-seventh Day of August, 2002

Attest:

Attesting Officer

JAMES E. ROGAN
*Director of the United States Patent and Trademark Office*